US012252555B2

(12) United States Patent
Cai et al.

(10) Patent No.: US 12,252,555 B2
(45) Date of Patent: Mar. 18, 2025

(54) SELENIUM-CHELATING PEA OLIGOPEPTIDE, AND PREPARATION METHOD AND USE THEREOF

(71) Applicant: CHINA NATIONAL RESEARCH INSTITUTE OF FOOD & FERMENTATION INDUSTRIES CO., LTD., Beijing (CN)

(72) Inventors: Muyi Cai, Beijing (CN); Ruizeng Gu, Beijing (CN); Jun Lu, Beijing (CN); Wenying Liu, Beijing (CN); Xiuyuan Qin, Beijing (CN); Xingchang Pan, Beijing (CN); Zhe Dong, Beijing (CN); Yong Ma, Beijing (CN); Yaguang Xu, Beijing (CN); Yongqing Ma, Beijing (CN); Liang Chen, Beijing (CN); Lu Lu, Beijing (CN); Haixin Zhang, Beijing (CN); Ying Wei, Beijing (CN); Yan Liu, Beijing (CN); Kelu Cao, Beijing (CN); Jing Wang, Beijing (CN); Guoming Li, Beijing (CN); Ming Zhou, Beijing (CN); Yuchen Wang, Beijing (CN); Yuqing Wang, Beijing (CN); Kong Ling, Beijing (CN); Yuan Bi, Beijing (CN); Xinyue Cui, Beijing (CN)

(73) Assignee: CHINA NATIONAL RESEARCH INSTITUTE OF FOOD & FERMENTATION INDUSTRIES CO., LTD., Beijing (CN)

( * ) Notice: Subject to any disclaimer, the term of this patent is extended or adjusted under 35 U.S.C. 154(b) by 0 days.

(21) Appl. No.: 17/227,206

(22) Filed: Apr. 9, 2021

(65) Prior Publication Data
US 2021/0230225 A1 Jul. 29, 2021

Related U.S. Application Data

(63) Continuation of application No. PCT/CN2018/121723, filed on Dec. 18, 2018.

(30) Foreign Application Priority Data

Oct. 12, 2018 (CN) .......................... 201811189889.7

(51) Int. Cl.
C07K 7/06 (2006.01)
(52) U.S. Cl.
CPC ...................................... C07K 7/06 (2013.01)
(58) Field of Classification Search
None
See application file for complete search history.

(56) References Cited

U.S. PATENT DOCUMENTS 6,136,598 A * 10/2000 Miller ..................... C12N 7/00
435/355
2012/0329716 A1 12/2012 Aluko

FOREIGN PATENT DOCUMENTS

| CN | 103194519 A | 7/2013 |
| CN | 104397428 A * | 3/2015 |
| CN | 104694341 A | 6/2015 |
| CN | 105603032 A | 5/2016 |
| CN | 106011211 A | 10/2016 |
| CN | 106075384 A | 11/2016 |
| CN | 106721060 A | 5/2017 |
| CN | 107279458 A | 10/2017 |
| CN | 108220371 A | 6/2018 |

OTHER PUBLICATIONS

CN104397428translation (retrieved from https://worldwide.espacenet.com/patent/search/family/052635150/publication/CN104397428A?q=cn104397428 on Oct. 5, 2022, 5 pages) (Year: 2015).*
Kreplak et al. ('A reference genome for pea provides insight into legume genome evolution' Nature Genetics v51 Sep. 2019 pp. 1411-1425) (Year: 2019).*
Blast search of PPKIYP (retrieved from https://blast.ncbi.nlm.nih.gov/Blast.cgi on Oct. 5, 2022, 35 pages) (Year: 2022).*
Zhu et al. ('Purification and characterization of antioxidative peptides prepared from pea protein with strong inhibitory activity on lipid oxidation' Reactive Oxygen Species v3(9) May 2017 pp. 208-217). (Year: 2017).*
Sterner et al. ('The Conservation of Mass' Nature Education Knowledge v3(10) 2011, retrieved from https://www.nature.com/scitable/knowledge/library/the-conservation-of-mass-17395478/#:~:text=Because%20elements%20are%20neither%20created,plant%20and%20into%20the%20atmosphere on May 28, 2024, 6 pages) (Year: 2011).*
The first Office Action of the parallel application JP2021-546031 2021.
"Natural enrichment of selenium in Saskatchewan field peas", Canadian Journal of Plant Science, 2010, vol. 90 , pp. 383-389.
(Continued)

Primary Examiner — Ronald T Niebauer
(74) Attorney, Agent, or Firm — J.C. PATENTS

(57) ABSTRACT

A selenium-chelating pea oligopeptide, a preparation method thereof and use thereof. After the selenium-chelating pea oligopeptide is subjected to digestion treatment in at least one of following three ways, a change rate of selenium content not more than 3% with respect to the selenium content before the digestion treatment: hydrolyzing for 4 hours by a pepsin at a pH value of 2 and a temperature of 37° C.; hydrolyzing for 6 hours by a trypsin at a pH value of 7.5 and a temperature of 37° C.; maintaining the temperature constant at 37° C., firstly hydrolyzing for 4 hours by the pepsin at a pH value of 2, and then continuing to hydrolyze for 6 hours by a trypsin at a pH value of 6.8. The preparation method thereof includes mixing and reacting an aqueous solution of pea oligopeptide and sodium selenite, and then being subjected to alcohol precipitation and drying.

7 Claims, 22 Drawing Sheets

Specification includes a Sequence Listing.

(56) References Cited

OTHER PUBLICATIONS

"Increase in the selenium content of the protein fraction of the seeds of garden pea (*Pisum sativum* L.) by the addition of selenium salts to the soil substrate", AGRIS, 2008, vol. 44, pp. 249-259.
"Selenoamino Acid-Enriched Green Pea as a Value-Added Plant Protein Source for Humans and Livestock", Plant Foods for Human Nutrition, 2017, vol. 72, pp. 168-175.
International Search Report for PCT/CN2018/121723 2022.
The first Office Action of the priority CN application 2022.
NPL1: "Preparation and Antioxidant Activity of Selenium-Chelating Soybean Peptides", Food Science, 2013, vol. 34, No. 16, pp. 27-32.
NPL2: "Preparation and stability of pea antioxidant peptides by enzymatic hydrolysis" Food and Oil, 2018, vol. 31, No. 1, pp. 16-18.
NPL3: "Research On Structure-Activity Relation Of The Polysaccharide Conjugate From Abalone Haliotis Hannai Ino" Abstracts of 13th Annual Meeting of CIFST, 2018.
NPL4: "Structure and composition of a potential antioxidant obtained from the chelation of pea oligopeptide and sodium selenite", Journal of Functional Foods 64(2020) 103619, pp. 1-8.
NPL5: "Study on Preparation of Fish Oil and Peptide Selenium Chelate from Red Sea Bream Head", Engineering Science and Technology, 2016, vol. 5, B024-379.
NPL6: "Study on preparation, structure and activity of soybean protein isolate peptide-Se complex", Food and Mechanics, 2018, vol. 34, No. 4, pp. 163-167.

\* cited by examiner

SELENIUM-CHELATING PEA OLIGOPEPTIDE, AND PREPARATION METHOD AND USE THEREOF

CROSS-REFERENCE TO RELATED APPLICATIONS

This application is a continuation of International Application No. PCT/CN2018/121723, filed on Dec. 18, 2018, which claims priority to Chinese Patent Application No. 201811189889.7, filed on Oct. 12, 2018, both of which are hereby incorporated by reference in their entireties.

TECHNICAL FIELD

The present disclosure relates to a selenium-chelating pea oligopeptide, and a preparation method and a use thereof and, in particular, to a selenium-chelating pea oligopeptide with high stability, capable of being effectively absorbed by a human body and having good oxidation resistance, and a preparation method and a use thereof.

BACKGROUND

A traditional metabolic model believes a protein must be hydrolyzed into amino acids before it can be absorbed and utilized by an organism; however, recent studies show that the animal's need for proteins also depends on a certain number of small molecule active peptides, and oligopeptides have specialized carriers and absorption channels in a human intestinal tract, and can enter a small intestine and be absorbed in a complete form.

A pea oligopeptide is a small molecule peptide obtained by enzymolysis or hydrolysis of a pea protein. It has been reported that the pea oligopeptide has antibacterial activity, antioxidant activity, ACE inhibitory activity and so on, and is a bioactive peptide widely used.

Selenium is one of trace elements that a human body must take from the outside world, and it plays an important role in maintaining human life activities. Studies have shown that selenium deficiency can lead to human hypoimmunity and also cause diseases such as Keshan disease.

At present, in addition to normal food intake, commonly used selenium supplementation methods include oral administration of inorganic seleniums such as sodium selenite. However, researches have been shown that an organic selenium has less toxicity and higher absorption rate than an inorganic selenium. Therefore, there have been reported studies about organic selenium products in the form of oligopeptide selenium such as soybean peptide selenium chelate, *Ganoderma lucidum* peptide selenium chelate, and fish head protein peptide selenium chelate, but chelation of pea oligopeptide and selenium is rarely reported. On the other hand, molecular stability of oligopeptide selenium (commonly known as chelated selenium) obtained by introducing selenium element into an oligopeptide molecule, whether the oligopeptide selenium is directly used as a product to ensure effective selenium supplementation, or the oligopeptide selenium is used as an intermediate raw material for further processing to ensure an expected effect of subsequent processing, is a concerned topic in the research of this type of product. But the selenium-chelating pea oligopeptide that can be effectively absorbed by and stably combined with the human body is even rarer.

SUMMARY

In view of the abovementioned defects in the prior art, the present disclosure provides a selenium-chelating pea oligopeptide, which has stable performance and can be effectively absorbed by the human body through the intestinal tract, so as to achieve effective selenium supplementation.

The present disclosure provides a preparation method of a selenium-chelating pea oligopeptide, the preparation method not only can obtain the selenium-chelating pea oligopeptide as described above, but also has advantages of high chelation rate and high yield.

The present disclosure further provides a use of the selenium-chelating pea oligopeptide in a health food.

In order to achieve the abovementioned object, the selenium-chelating pea oligopeptide provided by the present disclosure is subjected to digestion treatment in at least one of following three ways, and after that a change rate of selenium content is not more than 3% with respect to the selenium content before the digestion treatment:

hydrolyzing for 4 hours by a pepsin at a pH value of 2 and a temperature of 37° C.;

hydrolyzing for 6 hours by a trypsin at a pH value of 7.5 and a temperature of 37° C.;

maintaining the temperature constant at 37° C., firstly hydrolyzing for 4 hours by a pepsin at a pH value of 2, and then continuing to hydrolyze for 6 hours by a trypsin at a pH value of 6.8.

After the selenium-chelating pea oligopeptide (or known as selenium-chelating pea oligopeptide chelate) provided by the present disclosure is subjected to the abovementioned digestion treatment, the change rate (precisely, reduction rate) of selenium content is not more than 3% with respect to the selenium content before the digestion treatment. Further studies have shown that most of the selenium is combined with the pea oligopeptide by covalent bonds (or more precisely, coordinate bonds), and the covalent bonds between the two are relatively stable, so that selenium can stably pass through the stomach and intestinal tract with the pea oligopeptide, and is finally absorbed indirectly by complete absorption of the pea oligopeptide through small intestinal mucosa.

Furthermore, the selenium-chelating pea oligopeptide has good thermal stability, and after it is subjected to heat treatment at less than or equal to 100° C. for 2 hours, there is no significant difference in the selenium content compared with a control group before the heat treatment, and the change rate is not more than 3%; in other words, after a system of the selenium-chelating pea oligopeptide dispersed in water is subjected to treatment below 100° C. for 2 hours, the selenium content is more than 97% of the control group. The selenium-chelating pea oligopeptide not only can further ensure digestion and absorption of selenium in the human body, but also when used as an intermediate raw material for further processing, it can ensure an expected effect of subsequent processing.

Furthermore, the selenium-chelating pea oligopeptide has good acid-alkali stability, and after it is subjected to a treatment for 2 hours at a pH of 3-11 and a temperature of 37° C., the change rate of the selenium content is not more than 25% with respect to the control group before the treatment, in other words, after a system where the selenium-chelating pea oligopeptide is dispersed in water is subjected to an acidic, alkaline or neutral treatment for 2 hours, the selenium content is more than 75% with respect to the control group without the acidic and alkaline treatment. Good acid-alkali stability can further ensure digestion and absorption of selenium in the selenium-chelating pea oligopeptide in the human body, and can ensure the expected effect of subsequent processing when the selenium-chelating pea oligopeptide is used as an intermediate raw material for further selenium supplementation health products.

At the same time, the scavenging capacity of the selenium-chelating pea oligopeptide on DPPH free radicals and hydroxyl free radicals (OH) is greatly improved with respect to a pea oligopeptide as raw material; in addition, the selenium-chelating pea oligopeptide also has relatively strong antioxidant capacity and reducing capacity, and its reducing capacity is not a simple superposition of the pea oligopeptide and the sodium selenite, so that the selenium-chelating pea oligopeptide is very suitable for development as antioxidation health foods and selenium supplementation health foods.

In the selenium-chelating pea oligopeptide provided in some embodiments of the present disclosure, acid soluble protein content is more than 23%, total nitrogen content is more than 23%, indicating that molecular weights of proteins in the selenium-chelating pea oligopeptide are relatively low. Lower molecular weight proteins are more conducive to absorption by the human body.

Specifically, in some embodiments of the present disclosure, in the selenium-chelating pea oligopeptide, a proportion of components with a molecular weight of less than 1000 u is more than 85%, which is more conducive to absorption of selenium as the human body absorbs small molecule oligopeptides.

Furthermore, the selenium-chelating pea oligopeptide contains PPKIYP (SEQ ID NO:2, Pro-Pro-Lys-Ile-Tyr-Pro), it has been identified that PPKIYP is a peptide segment with a relatively strong antioxidant capacity.

After quantitative analysis, in the selenium-chelating pea oligopeptide, a mass content of the peptide segment PPKIYP (SEQ ID NO:2) is not less than 25 ng/mg, and generally 25-35 ng/mg.

Furthermore, the selenium-chelating pea oligopeptide further contains peptide segments TGRGAP (SEQ ID NO:1, Thr-Gly-Arg-Gly-Ala-Pro), HQMPKP (SEQ ID NO:3, His-Gln-Met-Pro-Lys-Pro) and TSSLP (SEQ ID NO:4, Thr-Ser-Ser-Leu-Pro).

After quantitative analysis, in the selenium-chelating pea oligopeptide, a mass content of TGRGAP (SEQ ID NO:1) is usually not less than 25 ng/mg, and generally 25-35 ng/mg; a mass content of HQMPKP (SEQ ID NO:3) is usually not more than 50 ng/mg, and is generally 40-50 ng/mg; a mass content of TSSLP (SEQ ID NO: 4) is generally 1-5 ng/mg.

Furthermore, in some embodiments of the present disclosure, the selenium content in the selenium-chelating pea oligopeptide is not less than 0.08 g/100 g; in other words, on average, per 100 g of the selenium-chelating pea oligopeptide, the mass of selenium element is more than or equal to 0.08 g, which can further ensure the effect of selenium supplementation.

In some embodiments of the present disclosure, the selenium-chelating pea oligopeptide can be a reaction product of an aqueous solution of pea oligopeptide and sodium selenite (Na2SeO3). Specifically, the aqueous solution of the pea oligopeptide is mixed with the sodium selenite, subsequently reacting for 20 minutes or more at 60-90° C., the obtained reaction product is then subjected to alcohol precipitation and drying to obtain the selenium-chelating pea oligopeptide.

The abovementioned pea oligopeptide is preferably selected from a pea oligopeptide in which contents of components with a molecular weight of less than 1000 u are more than 80%, and especially can be selected from a pea oligopeptide in which the contents of components with a molecular weight of less than 1000 u are more than or equal to 90%. In some embodiments of the present disclosure, the pea oligopeptide can be obtained by following preparation method: mixing a pea protein powder (with protein content of greater than 80%) and water in a material-to-liquid ratio of 1:8-12, adjusting a pH value of the resulting material liquid to 8-10, controlling a temperature to 40-60° C., and adding an alkaline protease and a neutral protease for enzymolysis, where dosages of the both enzymes are 1.0-3.0% of the mass of the pea protein powder, and enzymolysis time is 3-6 hours. After the enzymolysis is completed, the material liquid is subjected to enzyme deactivation, centrifugal separation, ceramic membrane filtration (pore size of a ceramic membrane is 50-200 nm), vacuum concentration, sterilization, and finally spraying and drying to obtain a powder, so as to obtain a pea oligopeptide powder.

The present disclosure further provides a preparation method of a selenium-chelating pea oligopeptide, including: mixing an aqueous solution of a pea oligopeptide with a sodium selenite, and then reacting a resulting mixed system for 20 minutes or more at 60-90° C., the obtained reaction product is then subjected to alcohol precipitation and drying to obtain the selenium-chelating pea oligopeptide.

As detected through UV full-wavelength scanning, scanning electron microscopy, Fourier infrared spectroscopy and other means, the pea oligopeptide and the sodium selenite undergo the abovementioned reaction to obtain a new chelate. It is speculated that the selenium in the sodium selenite is stably combined with the pea oligopeptide by covalent bonds. It may be that the selenium ion ($Se^{4+}$) binds to carboxyl and amino groups in the pea oligopeptide by coordinate bonds. In other words, $Se^{4+}$ provides a 4d empty orbital, and O and N provide lone pairs of electrons, which each can occupy the 4d empty orbital to form a stable coordinate bond, so that the selenium-chelating pea oligopeptide has good thermal stability, acid-alkali stability and in vitro digestion stability, ensuring that the selenium can enter the intestine smoothly and be absorbed indirectly through intake of the oligopeptide by intestinal mucosa, thereby achieving the effect of selenium supplementation; and so that when the obtained pea oligopeptide selenium is used as an intermediate raw material for further processing, it can ensure the expected effect of subsequent processing.

It is for the above reasons, the abovementioned reaction can be called "chelation reaction", and the obtained selenium-chelating pea oligopeptide can also be called "selenium-chelating pea oligopeptide chelate" or "pea oligopeptide chelated selenium", etc., according to the usual name in the field, where a binding rate of the selenium and the pea oligopeptide is also indicated as "chelation rate".

Temperature has a great influence on the reaction between the pea oligopeptide and the sodium selenite, and as the temperature rises, both the chelation rate and the yield of the selenium-chelating pea oligopeptide show a trend of increasing firstly and decreasing subsequently. In a specific implementation process of the present disclosure, a reaction temperature is generally controlled to be 70-90° C., and further 80-85° C., so as to obtain higher chelation rate and yield at the same time.

In some embodiments of the present disclosure, a mass ratio (peptide-salt mass ratio) of the pea oligopeptide to the sodium selenite is generally controlled to be 1-5:1. In a process of a chemical reaction, a relative ratio of reactants may affect formation of some steric bonds. Specifically, in some embodiments of the present disclosure, as the ratio of the pea oligopeptide to the sodium selenite increases (e.g., increasing from 1:1 to 5:1), the chelation rate gradually decreases, while the yield of the selenium-chelating pea oligopeptide increases firstly and decreases subsequently. Comprehensively considering the chelation rate and the yield, the mass ratio of the pea oligopeptide to the sodium selenite is generally controlled to be 2-4:1.

In some embodiments of the present disclosure, in the aqueous solution of the pea oligopeptide, a concentration of the pea oligopeptide (peptide concentration) is generally controlled to be 1-5 g/100 mL. With an increase of the peptide concentration, both the chelation rate and the selenium-chelating pea oligopeptide show a trend of increasing firstly, stabilizing subsequently, and then decreasing. Comprehensively considering the chelation rate and the yield, the peptide concentration is generally controlled to be 3-5 g/100 mL.

Reasonable control of the pH value of the mixed system of the pea oligopeptide and the sodium selenite is beneficial for obtaining higher chelation rate and yield. In some embodiments of the present disclosure, the chelation reaction is generally carried out under a weak alkaline condition, for example, the pH value is controlled to be 7.5-9. Since the pH value of the mixed system is about 8 when the pea oligopeptide and the sodium selenite are completely dissolved, the pH value may not be adjusted, or the pH value may be adjusted by such as adding NaOH or acetic acid before the reaction.

Reasonable control of reaction time is also beneficial for obtaining the highest chelation rate and yield. In general, with prolongation of the reaction time, both the chelation rate and the yield show a trend of increasing firstly, decreasing subsequently, and gradually becoming stable finally. In a specific implementation process of the present disclosure, comprehensively considering the chelation rate and the yield, as well as time costs, the reaction time is generally controlled to be 20 min-60 min.

It can be understood that a molecular weight distribution of the pea oligopeptide used as a reaction raw material would also affect a final molecular weight distribution of the selenium-chelating pea oligopeptide. In a specific implementation process of the present disclosure, in the selected pea oligopeptide, contents of components with a molecular weight of less than 1000 u are preferably more than 80%, preferably more than or equal to 90%.

In some embodiments of the present disclosure, the pea oligopeptide is obtained by the following preparation method: mixing a pea protein powder (with a protein content of greater than 80%) and water in a material-to-liquid ratio of 1:8-12, adjusting a pH value of a material liquid to 8-10, controlling a temperature to 40-60° C., and adding an alkaline protease and a neutral protease for enzymolysis; where dosages of the both enzymes are 1.0-3.0% of the mass of the pea protein powder, and enzymolysis time is 3-6 hours. After the enzymolysis is completed, the material liquid is subjected to enzyme deactivation, centrifugal separation, ceramic membrane filtration (pore size of a ceramic membrane is 50-200 nm), vacuum concentration, sterilization, and finally spraying and drying to obtain a powder, so that a pea oligopeptide powder meeting above requirements can be prepared.

The present disclosure further provides a use of the abovementioned selenium-chelating pea oligopeptide in a health food. As described above, since the selenium-chelating pea oligopeptide has good stability, can enter the intestine smoothly and be absorbed indirectly through intake of the oligopeptide by intestinal mucosa, thereby achieving the effect of selenium supplementation, the selenium-chelating pea oligopeptide can be used as a novel selenium supplementation preparation, and developed as a nutritional and functional food suitable for selenium-deficient people, for example, adding it into milk powder or other health food, or using as an intermediate raw material for further processing to obtain a health food; in addition, since the scavenging capacity of the selenium-chelating pea oligopeptide on DPPH free radicals and hydroxyl free radicals is greatly improved with respect to a pea oligopeptide as a raw material, and the selenium-chelating pea oligopeptide has relatively strong reducing capacity and antioxidant capacity, it is very suitable for being developed as an antioxidation health food and an antioxidation selenium supplementation food.

In the selenium-chelating pea oligopeptide provided by the present disclosure, the selenium is stably combined with the pea oligopeptide in a way of covalent bonds, with strong binding force, and can have good stability for different digestion ways; after hydrolyzed by a pepsin and a trypsin, the selenium content is reduced slightly, thus the selenium can enter the intestine smoothly and be absorbed indirectly through intake of the oligopeptide by intestinal mucosa, thereby achieving effects of selenium supplementation, and the selenium can be applied to selenium supplementation health food, and used as an intermediate raw material for processing to obtain an expected product.

Furthermore, in the selenium-chelating pea oligopeptide, a proportion of components with molecular weight less than 1000 u is more than 85%, and the selenium content is not less than 0.08 g/100 g, which can further improve effects of selenium supplementation.

In addition, the scavenging capacity of the selenium-chelating pea oligopeptide on DPPH free radicals and OH free radicals is greatly improved with respect to a raw material pea oligopeptide; the selenium-chelating pea oligopeptide further has relatively strong antioxidant capacity and reducing capacity, therefore, the selenium-chelating pea oligopeptide can be applied to antioxidation health food.

The preparation method of a selenium-chelating pea oligopeptide provided by the present disclosure not only enables the selenium to be bound with the oligopeptide by stable covalent bonds in the prepared selenium-chelating pea oligopeptide, ensuring that the selenium-chelating pea oligopeptide has good thermal stability, acid-alkali stability and digestion stability, but also makes the selenium-chelating pea oligopeptide have relatively strong antioxidant capacity and reducing capacity, and the reducing capacity is not a simple superposition of the chelated raw peptide and the sodium selenite, but the reducing capacity is increased by the preparation method.

At the same time, use of the preparation method further makes the selenium-chelating pea oligopeptide have following advantages: moisture content is low, generally 14.17%=1.12%, which can inhibit most of molds and staphylococci and is convenient for storage; acid soluble protein content is more than 23%, total nitrogen content is more than 23%, indicating that molecular weights of proteins in the selenium-chelating pea oligopeptide are relatively low; the proportion of molecular weight distributions below 1000 u is more than 85%, wherein most of them are 500 u or less, thus it is very conducive to absorption by the human body; the selenium content is 0.08 g/100 g or more, which can ensure effect of selenium supplementation.

DESCRIPTION OF EMBODIMENTS

Figure 1:
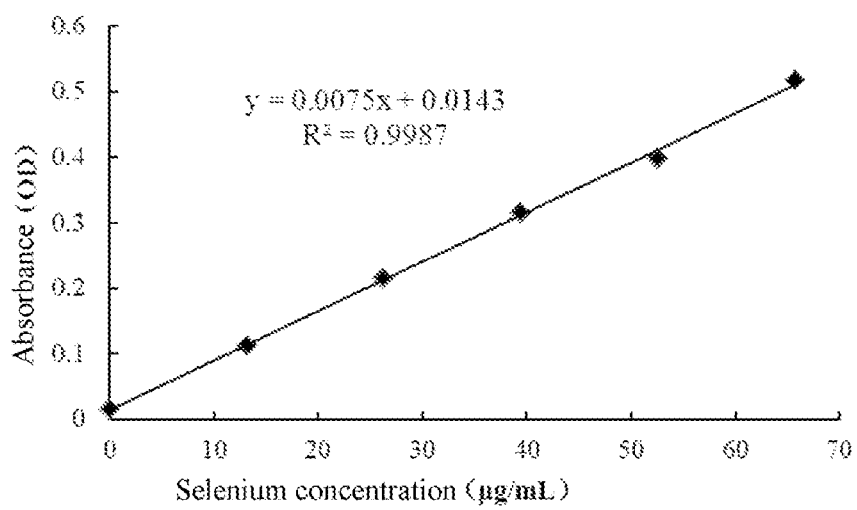
FIG. 1 is a standard curve of selenium drawn for determination of selenium content in the present disclosure.

The technical solutions in the embodiments of the present disclosure will be described clearly and completely in combination with accompanying drawings of the embodiments of the present disclosure hereinafter. Obviously, the embodiments described are a part of embodiments of the present disclosure, and are not all embodiments.

The raw material information used in the following examples and experimental examples are listed below:

Pea Oligopeptide: self-made; Sodium Selenite: Analytical Reagent, purchased from Tianjin Damao Chemical Reagent Factory; 3'3-Diaminobenzidine (DAB 4HCl): Reagent grade; Disodium ethylenediamine tetraacetate (EDTA-2Na), Biotechnological grade, from Biotopped Amresco; Hydrobromic Acid: Analytical Reagent, from Tianjin Fuchen Chemical Reagent Factory; Hydroxylamine Hydrochloride, Perchloric Acid, Nitric Acid, Hydrochloric Acid, Sodium Hydroxide, 95% Ethanol, Toluene, Trichloroacetic Acid: Analytical Reagent, all purchased from Beijing Chemical Factory; Pepsin, Trypsin: from Nanning Pangbo Biological Co., Ltd.; Trifluoroacetic Acid: Analytical Reagent, from Alfa Aesar Company; Acetonitrile: Chromatographic Pure, from Fisher Company; 1,1-Diphenyl-2-Trinitrophenylhydrazine (DPPH), from Sigma Company (USA); Ultrapure Water, self-made in laboratory.

The pea oligopeptide is specifically prepared by the following process:

mixing pea protein powder (protein content is about 82%) and purified water in a material-to-liquid ratio of about 1:10 to make a slurry, and after stirring until uniform, adding sodium hydroxide (food grade) to adjust a pH value of the slurry to about 9, controlling a temperature to 50±2° C., and adding Alcalase 2.4 L (2.5%, w/w) and Neutrase 0.8 L (1.5%, w/w), both proteases are purchased from Novozymes Biotechnology Co., Ltd.; the enzymolysis time is about 4.5 hours. After the enzymolysis time is over, the material liquid is heated to 120±2° C. through a plate heat exchanger for about 20 s; the material liquid after enzyme deactivation is subjected to centrifugal separation, ceramic membrane filtration, vacuum concentration, sterilization, and then spraying and drying to obtain a powder, so that the pea oligopeptide powder can be prepared.

Using high performance gel filtration chromatography described in literature Antioxidant Effects of Corn Oligopeptide in vitro, LIU Wenying, LIN Feng, JIN Zhentao, etc., [J]. Food Science, 2011, 32 (5): 22-26), the molecular weight and distribution thereof of the pea oligopeptide are determined through percentages of peak areas, wherein, a proportion of components with molecular weight >5000 u is 0; a proportion of components with molecular weight of 2000-5000 u is 0.95%; a proportion of components with molecular weight of 1000-2000 u is 7.79%; a proportion of components with molecular weight of 500-1000 u is 25.25%; a proportion of components with molecular weight of 140-500 u is 60.50%; a proportion of components with molecular weight <140 u is 5.51%. Through calculation, a proportion of components with molecular weight less than 1000 u is 91.26%.

The instrument information used in the following examples and experimental examples are listed below:

EL20 pH meter, from Mettler Toledo; KQ-250E ultrasonic shaker, Kunshan Ultrasonic Instrument Co., Ltd.; 1204007 thermostat water bath, from Suzhou Percival Laboratory Equipment Co., Ltd.; microplate reader, from Dynex Spectra Mr; DHG-9075A electro-thermostatic blast dryer, from Beijing Luxi Technology Co., Ltd.; versatile electric stove, from Beijing Kewei Yongxing Instrument Co., Ltd.; LC-20AD type high performance liquid chromatograph, from Shimadzu Corporation (Japan); F30200150 Kjeldahl nitrogen determination apparatus, Velp Scientifica Company.

In the following examples and experimental examples, the detection and evaluation methods for the selenium-chelating pea oligopeptide are listed as follows:

1. Determination of Molecular Weight Distribution

It is determined by high performance gel filtration chromatography. 5 kinds of peptide standards, which are glycine-glycine-glycine (molecular weight 189), glycine-glycine-tyrosine-arginine (SEQ ID NO:5, molecular weight 451), bacitracin (molecular weight 1450), aprotinin (molecular weight 6500) and cytochrome C (molecular weight 12500), are used to prepare 0.1% (M/V) solutions, respectively; after filtering samples with a polytetrafluoroethylene filter membrane of 0.2 u m pore size, the samples are injected, and gel filtrations are performed through the high performance liquid chromatograph, and relative molecular weight calibration curves are prepared. Mobile phase: V (acetonitrile) V (water):V (trifluoroacetic acid)=45:55:0.1; injection volume: 10 µL; flow rate: 0.5 mL/min; detection wavelength: 220 nm; column temperature: 30° C.; an ultraviolet detector is used for detecting, and GPC software is used to process data. The chromatographic data of the samples are substituted into equations of the calibration curves for calculation, thereby obtaining peptide molecular weight and its distribution range of the sample. A peak area normalization method can be used to calculate relative percentage of peptides in different molecular weight ranges.

2. Determination of Selenium Content 2.190 g of $Na_2SeO_3 \cdot 5H_2O$ is accurately weighed, and dissolved in a small amount of ultrapure water, and then 48% hydrobromic acid is added, and then diluted to 1 L with ultrapure water, so as to prepare a selenium standard stock solution (657.4746 mg/L).

1 mL of the selenium standard stock solution is drawn, diluted to 100 mL with ultrapure water, so as to prepare a selenium standard working solution (6.57 µg/mL).

0, 2, 4, 6, 8, 10 mL of the selenium standard working solutions are accurately measured and taken, and after digested with an acid, absorbance at 420 nm of a yellow complex produced by a reaction of 3'3-diaminobenzidine and reduced selenium is measured, with specific operation method referring to a spectrophotometric method proposed in literature (Chen Fu, Jia Shanshan, Zhu Lianqin, etc., Determination of Selenium by 3'3-Diaminobenzidine Spectrophotometric Method [C]. Domestic animal medicine Branch Conference and Annual Seminar, Chinese Association of Animal Science and Veterinary Medicine, 2011).

The selenium concentration is used as the horizontal coordinate and the absorbance is used as the vertical coordinate to draw a standard curve of selenium, as shown in FIG. 1.

A certain amount of a sample to be tested is accurately weighed, and is dissolved in 10 mL of ultrapure water, then the sample is treated with the above method, and then the absorbance after the treatment is measured. The selenium content is determined by referring to the standard curve.

3. Chelation Rate and Yield

A calculation formula of the chelation rate is:

Chelation rate (%)=m1/m2×100%, wherein, m1 is the selenium content in the selenium-chelating pea oligopeptide (mass of selenium element in the selenium-chelating pea oligopeptide), m2 is mass of selenium element in the sodium selenite.

A calculation formula of the yield of a chelate is:

Yield (%)=m3/m4×100%, where m3 is mass of chelated product, m4 is mass of all substances added to chelating system.

4. Determination of Basic Physicochemical Property

Moisture content in selenium-chelating pea oligopeptide is determined using the national standard method GB 5009.3-2010. Total nitrogen (protein) content in selenium-chelating pea oligopeptide is determined using the national standard method GB 5009.5-2010. Content of acid soluble protein in selenium-chelating pea oligopeptide is determined by referring to the national standard method GB 22729-2008.

5. Thermal Stability Experiment

A selenium-chelating pea oligopeptide sample is dissolved in ultrapure water, so as to prepare a solution with a concentration of 2 mg/mL. 30 mL of the solution is taken into centrifuge tubes, which are subjected to thermostatic water bath at 25, 40, 60, 80, 100° C. for 2 h, respectively, where 25° C. is a control group at room temperature. Afterwards, it is cooled to room temperature, and the molecular weight distribution is detected; a sample of 3 mL is placed in a dialysis bag and dialyzed for 60 hours to detect the selenium content.

6. Acid-Alkali Stability Experiment

A selenium-chelating pea oligopeptide sample is dissolved in ultrapure water, so as to prepare a solution with a concentration of 2 mg/mL, 30 mL of the solution is taken into centrifuge tubes, pHs of the tubes are adjusted to 3, 5, 7, 9, 11 with HCl (1 mol/L) and NaOH (1 mol/L) respectively, and then the tubes are placed into a constant temperature water bath at 37° C. for 2 h, and at the same time, an untreated control group is set, and the molecular weight distribution is detected after cooling to room temperature; a sample of 3 mL is placed in a dialysis bag and dialyzed for 60 hours to detect the selenium content.

7. In Vitro Simulation Experiment of Gastrointestinal Digestive Tract 7.1 Pepsin Digestion Experiment A selenium-pea oligopeptide chelate sample is dissolved in ultrapure water, so as to prepare a solution with a concentration of 2 mg/mL, 40 mL of the solution is taken into a centrifuge tube. The pH of the solution is adjusted to 2 with HCl (1 mol/L), and then the solution is preheated in constant temperature water bath at 37° C. for 20 min. Afterwards, 6% % (material ratio) of a pepsin is added, and after mixing evenly, 20 mL is quickly taken out and placed into another centrifuge tube, treated in a boiling water bath at 100° C. for 10 minutes, serving as a control before digestion. The remaining is placed in a constant temperature water bath at 37° C. for 4 h, and then the enzyme is deactivated in a boiling water bath at 100° C. The molecular weight distribution is detected after cooling at room temperature; and a sample of 3 mL is placed in a dialysis bag and dialyzed for 60 hours to detect the selenium content, denoted by M'. For the solution serving as the control before digestion, a sample of 3 mL is placed in a dialysis bag and dialyzed for 60 hours to detect the selenium content, denoted by M. A mass of selenium decomposed during the digestion treatment by the pepsin is M-M'. Therefore, a change rate of the selenium content is a mass percentage of the mass of selenium decomposed during the digestion treatment by the pepsin to a total mass of selenium in the selenium-pea oligopeptide chelate before the digestion treatment, denoted by (M−M')/M.

7.2 Trypsin Digestion Experiment

A selenium-pea oligopeptide chelate sample is dissolved in ultrapure water, so as to prepare a solution with a concentration of 2 mg/mL, 40 mL of the solution is taken into a centrifuge tube. The pH of the solution is adjusted to 7.5 with NaOH (1 mol/L), and then the solution is preheated in constant temperature water bath at 37° C. for 20 min. 2%‰ (material ratio) of a trypsin is added, and after mixing evenly, 20 mL is quickly taken out and placed into another centrifuge tube, treated in a boiling water bath at 100° C. for 10 minutes, serving as a control before digestion. The remaining is placed in a constant temperature water bath at 37° C. for 6 h, and then the enzyme is deactivated in a boiling water bath at 100° C., the molecular weight distribution is detected after cooling at room temperature; and a sample of 3 mL is placed in a dialysis bag and dialyzed for 60 hours to detect the selenium content, denoted by M'. For the solution serving as the control before digestion, a sample of 3 mL is placed in a dialysis bag and dialyzed for 60 hours to detect the selenium content, denoted by M. A mass of selenium decomposed during the digestion treatment by the trypsin is M−M'. Therefore, a change rate of the selenium content is a mass percentage of the mass of selenium decomposed during the digestion treatment by the trypsin to a total mass of selenium in the selenium-pea oligopeptide chelate before the digestion treatment, denoted by (M−M')/M.

7.3 Pepsin Digestion Experiment Followed by Trypsin Digestion Experiment

After performing pepsin digestion according to the method as described in 7.1 pepsin digestion experiment, the pH is adjusted to 6.8 with NaOH (1 mol/L), preheating in constant temperature water bath at 37° C. for 20 min, 2‰ (material ratio) of a trypsin is added, and after mixing evenly, 20 mL is quickly taken out and placed into another centrifuge tube, treated in a boiling water bath at 100° C. for 10 minutes, serving as a control before digestion. The remaining is placed in a constant temperature water bath at 37° C. for 6 h, and then the enzyme is deactivated in a boiling water bath at 100° C., the molecular weight distribution is detected after cooling at room temperature; and a sample of 3 mL is placed in a dialysis bag and dialyzed for 60 hours to detect the selenium content, denoted by M'. For the solution serving as the control before digestion as described in 7.1, a sample of 3 mL is placed in a dialysis bag and dialyzed for 60 hours to detect the selenium content, denoted by M. A mass of selenium decomposed during the digestion treatment by the pepsin and the trypsin is M−M'. Therefore, a change rate of the selenium content is a mass percentage of the mass of selenium decomposed during the digestion treatment by the pepsin and the trypsin to a total mass of selenium in the selenium-pea oligopeptide chelate before the digestion treatment, denoted by (M−M')/M.

8. Antioxidant Function Evaluation 8.1 Determination of Capacity to Scavenge DPPH Free Radicals Samples in different concentrations are taken and mixed with DPPH-anhydrous ethanol solution (0.1 mol/L) in a volume ratio of 1:1, and stored for 30 min under a dark condition, and the absorbance of the mixed solution is measured at 517 nm in ultraviolet-visible spectrum, and recorded as $A_i$. Correspondingly, sample solutions in different mass concentrations are evenly mixed with anhydrous ethanol solution in a volume ratio of 1:1, and stored for 30 min under a dark condition at room temperature, and the absorbance of the mixed solution is measured at 517 nm in ultraviolet-visible spectrum, and recorded as $A_j$. Distilled water is evenly mixed with DPPH-anhydrous ethanol solution (0.1 mol/L) in a volume ratio of 1:1, and stored for 30 min under a dark condition at room temperature, and the absorbance is measured at 517 nm in ultraviolet-visible spectrum, and recorded as $A_c$. Experiment of each group is repeated three times, and average values are obtained and standard deviations are calculated. The sodium selenite and the pea oligopeptide are used as raw material controls before chelation, and ascorbic acid is used as a positive control, the scavenging rate of the sample on DPPH free radicals is calculated according to the following formula:

Scavenging Rate $$(\%) = \left(1 - \frac{A_i - A_j}{A_c}\right) \times 100\%$$

8.2 Determination of Capacity to Scavenge OH Free Radicals

Sample solutions in different concentrations are taken and evenly mixed with $FeSO_4$ (5 mol/L) and salicylic acid-anhydrous ethanol solution (5 mol/L) in a volume ratio of 1:2:2, the reaction is started with 1 volume of $H_2O_2$ solution (5 mol/L), reacting in a water bath at 37° C. for 1 h, and the absorbance is measured at 510 nm in ultraviolet-visible spectrum, and recorded as $A_2$. Correspondingly, the $H_2O_2$ solution (5 mol/L) is replaced with 1 volume of water, and the ratio of remaining reagents remains unchanged, reacting in a water bath at 37° C. for 1 h, and the absorbance is measured at 510 nm in ultraviolet-visible spectrum, and recorded as $A_{20}$. The sample solution is replaced with distilled water, and the ratio of remaining reagents remains unchanged, reacting in a water bath at 37° C. for 1 h, and the absorbance is measured at 510 nm, and recorded as $A_{02}$. Experiment of each group is repeated three times, and average values are obtained and standard deviations are calculated. The sodium selenite and the pea oligopeptide are used as raw material controls before chelation, and ascorbic acid is used as a positive control, the scavenging rate of the sample on OH free radicals is calculated according to the following formula:

Scavenging Rate $$(\%) = \left(1 - \frac{A_2 - A_{20}}{A_{02}}\right) \times 100\%$$

8.3 Determination of Reducing Capacity

Sample solutions in different concentrations are taken and evenly mixed with phosphate buffer (0.2 mol/L, pH 6.6) and $K_3[Fe(CN)_6]$ solution with a mass concentration of 1% in a volume ratio of 1:1:1, stored in a water bath at 50° C. for 10 min, and quickly cooled with cold water. 1 volume of trichloroacetic acid solution with a mass concentration of 10% is added, shaken well quickly and thoroughly under a dark condition, and then 1 volume of reaction mixture is taken out, and added with 1 volume of distilled water and 0.2 volume of FeCl$_3$ solution with a mass concentration of 0.1%, and after shaking well quickly and thoroughly under a dark condition, standing for 10 min, the absorbance is measured at 700 nm, and recorded as A$_3$. The sodium selenite and the pea oligopeptide are used as raw material controls before chelation, and ascorbic acid is used as an overall control, the absorbance A$_3$ is directly used as a parameter of the reducing capacity of the sample. Experiment of each group is repeated three times, and average values are obtained and standard deviations are calculated.

9. Identification of Peptide Segments and Identification of Antioxidant Capacity 9.1 Identification of Peptide Segments (1) LC-MS/MS Setting Liquid chromatography-tandem mass spectrometry is used to analyze peptide segments, the liquid chromatography is set with the following parameters for separation:

A sample concentration is: 5 mg/mL, an Ultimate 3000 HPLC liquid system connected to a Q Exactive mass spectrometer (LC-MS/MS, Thermo Scientific Company) is used for gradient elution for 30 minutes, with flow rate of 0.30 μL/min. The analytical column is a self-made quartz capillary (an inner diameter is 75 μm, a column length is 15 cm, Upchurch, Oak Harbor, WA) containing C18 packings (300 Å, 5 μm, Varian, Lexington, MA). Mobile phase A is 0.1% of formic acid in water, mobile phase B contains 80% of acetonitrile and 0.1% of formic acid.

The Q Exactive mass spectrometer uses an Xcalibur 2.1.2 software data dependent acquisition method, primary detection type is orbitrap, mass range of primary full scan is 100-1200 m/z, with resolution being 70,000, ions with signal intensity of top 20 are selected for secondary fragmentation, secondary detection type is ion trap, with resolution being 17500, collision energy is 27%.

(2) Processing of Data

Original data of mass spectrum are obtained by using database and de novo sequencing of peptide segment (de novo method), respectively, and peptide segment obtained in database is compared with suspicious peptide segment obtained by using PEAKS search library.

Proteome Discovery software (Version PD1.4, Thermo-Fisher Scientific, USA) is used for database search, search conditions are: no enzyme digestion, dynamic modification includes: oxidation (M); mass deviation of parent ions is set as 20 ppm, secondary mass deviation is set as 0.02 Da, Percolator of PD library is used to calculate an FDR value, FDR represents false positive rate of peptide segment. When q value is less than 1%, spectrum matching of the peptide segment can be considered correct. The peptide segment designated as a given protein can be considered unique. In protein identification, the false positive rate is set as 0.01.

(3) Synthesis of Peptide Segment

Peptide segment standard is provided by GL Biochem (Shanghai) Co., Ltd. A synthesis route of a peptide segment is: selecting FMOC-ARG (PBF)-WANG RESIN resin→removing FMOC on the resin by hexahydropyridine→reacting by using HOBT and DIC as condensing agents and adding second amino acid FMOC-CYS (TRT)-OH→after completion of the reaction, continuing to remove FMOC, connecting the next amino acid, and cycling until the last amino acid is connected→treating the prepared resin with TFA solution to obtain a crude polypeptide→dissolving the crude polypeptide and adding proportioned glutathione, stirring at low temperature and performing MS every 6-12 hours to confirm oxidation state, and at the same time, using a mercapto detection agent to assist in determining whether oxidation is complete→after the oxidation is complete, sending for purification to obtain a standard synthetic peptide segment (synthetic peptide segment standard).

9.2 Identification of Oxidation Resistance of Peptide Segment

ABTS+ method is utilized to identify the oxidation resistance of the selenium-chelating pea oligopeptide and peptide segment, Trolox is utilized as antioxidant standard substance to draw a standard curve, the prepared standard synthetic peptide segment (5 mg/mL) and selenium-chelating pea oligopeptide (5 mg/mL) each are reacted with an ABTS kit (Biyuntian), the absorbance is measured at 734 nm, to investigate their antioxidant capacity.

9.3 Quantitative Analysis of Peptide Segment

Quantitative analysis of peptide segment of the selenium-chelating pea oligopeptide is performed, specific instrument conditions are as follows:

(1) Instrument and Reagent Information

Instrument type: HPLC-MS/MS (liquid chromatography (LC): Dionex Corporation Ultimate3000—mass spectrum (MS): AB Company (USA): API 3200 Q TRAP); methanol, acetonitrile, etc. are purchased from Fisher Company.

(2) Pretreatment of Sample

A proper amount of distilled water and an equal volume of protein precipitation agent (acetonitrile, containing 100 ng/ml of internal standard) are added, vortexed for 2 min, sonicate for 2 min, centrifuged at 13200 rpm for 4 min, and a supernatant is taken to be tested.

(3) Lc Conditions:

Chromatographic column: MSLAB HP-C18 (150*4.6 mm, 5 μm, 120a); column temperature: 50° C.; flow rate: 1 mL/min;

mobile phase: aqueous phase A: water (2 MMOL/L ammonium formate); organic phase B: acetonitrile (2 MMOL/L ammonium formate);

Injection volume: 10 μL;

Gradient: 0-2 min: 95% A+5% B; 2.1-5.0 min: 20% A+80% B; 5.1-7 min: 0% A+100% B; 7.1-10 min: 95% A+5% B.

(3) Ms Conditions:

ion source: +ESI electrospray ion source; scanning mode: MRM multiple reaction monitoring; CUR: 20 psi (air curtain gas); IS: +4500V (spray voltage); CAD: Medium (collision gas); CXP: 2.0 (ejection voltage of collision chamber); GS1: 45 psi (atomizing gas); TEM: 550° C. (atomizing temperature); EP: 10 (injection voltage); GS2: 50 psi (auxiliary gas)

10. Statistical Treatment

The experimental data is statistically processed with SPSS 13.0 software, and the comparison between groups is performed by t-test, if P<0.05, there will be a significant difference between two groups.

Example 1

5 g of pea oligopeptide was dissolved in 100 mL of ultrapure water, so as to prepare a pea oligopeptide aqueous solution (5 g/100 mL), and then 2.5 g of sodium selenite was added to it, mixing thoroughly in an ultrasonic shaker. The pH was adjusted to 9.0, reaction was carried out in a constant temperature water bath at 80° C. for 30 min, and then immediately 95% ethanol with 4 times the volume of ultrapure water was poured, standing for overnight. The supernatant was discarded, and the remaining was dried in a constant temperature blast dry oven at 35° C. to obtain a selenium-chelating pea oligopeptide.

Example 2

4 g of pea oligopeptide was dissolved in 100 mL of ultrapure water, so as to prepare a pea oligopeptide aqueous solution (4 g/100 mL), and then 2 g of sodium selenite was added to it, mixing thoroughly in an ultrasonic shaker. The pH was adjusted to 8.0, reaction was carried out in a constant temperature water bath at 85° C. for 30 min, and then immediately 95% ethanol with 4 times the volume of ultrapure water was poured, standing for overnight. The supernatant was discarded, and the remaining was dried in a constant temperature blast dry oven at 35° C. to obtain a selenium-chelating pea oligopeptide.

Example 3

5 g of pea oligopeptide was dissolved in 100 mL of ultrapure water, so as to prepare a pea oligopeptide aqueous solution (5 g/100 mL), and then 1.67 g of sodium selenite was added to it, mixing thoroughly in an ultrasonic shaker. The pH was adjusted to 8.0, reaction was carried out in a constant temperature water bath at 90° C. for 30 min, and then immediately 95% ethanol with 4 times the volume of ultrapure water was poured, standing for overnight. The supernatant was discarded, and the remaining was dried in a constant temperature blast dry oven at 35° C. to obtain a selenium-chelating pea oligopeptide.

Example 4

3 g of pea oligopeptide was dissolved in 100 mL of ultrapure water, so as to prepare a pea oligopeptide aqueous solution (3 g/100 mL), and then 1.5 g of sodium selenite was added to it, mixing thoroughly in an ultrasonic shaker. The pH was adjusted to 8.5, reaction was carried out in a constant temperature water bath at 90° C. for 30 min, and then immediately 95% ethanol with 4 times the volume of ultrapure water was poured, standing for overnight. The supernatant was discarded, and the remaining was dried in a constant temperature blast dry oven at 35° C. to obtain a selenium-chelating pea oligopeptide.

The selenium-chelating pea oligopeptide in the above Examples 1~4 was tested, where basic physicochemical properties are shown in Table 1. It can be seen from Table 1 that the basic physicochemical properties of the selenium-chelating pea oligopeptide obtained in Examples 1~4 were relatively similar, the acid soluble protein content was more than 23%, the total nitrogen content was more than 23%, the acid soluble protein accounted for more than 97% of the crude protein, indicating that molecular weights of proteins in the selenium-chelating pea oligopeptide were all low, which is good for absorption by the human body.

In Examples 1-4, the moisture content of the selenium-chelating pea oligopeptide was within a range of 14.17%±1.12%. This moisture content was equivalent to 15-17% moisture in wheat flour, a corresponding aw value was 0.80-0.87, most of molds and staphylococci can be inhibited, thus being convenient for storage.

As shown in Table 1, in Examples 1-4, the selenium contents in the selenium-chelating pea oligopeptide were all above 0.08 g/100 g, indicating that the selenium-chelating pea oligopeptide products with high selenium content can be obtained. In further calculation, using the methods of Examples 1-4, the chelation rates of the selenium-chelating pea oligopeptide were more than 20%, and even more than 50%; at the same time, the yields of the selenium-chelating pea oligopeptide were more than 10%, and even more than 30%.

TABLE 1

Basic physicochemical properties, selenium contents, chelation rates and yields of selenium-chelating pea oligopeptide

| NO. | Acid soluble protein content | Total nitrogen content | Selenium content | Chelation rate | Yield |
|---|---|---|---|---|---|
| Example 1 | 23.22% ± 0.12% | 23.87% ± 0.30% | 0.65 g/100 g | 57.23% | 27.87% |
| Example 2 | 23.15% ± 0.16% | 23.46% ± 0.27% | 0.18 g/100 g | 24.33% | 19.47% |
| Example 3 | 23.37% ± 0.15% | 23.52% ± 0.36% | 0.08 g/100 g | 29.69% | 10.07% |
| Example 4 | 23.25% ± 0.19% | 23.85% ± 0.28% | 0.23 g/100 g | 24.33% | 33.46% |

The specific molecular weight distribution of the selenium-chelating pea oligopeptide prepared in Examples 1~4 was shown in Table 2. Where a gel chromatogram of molecular weight distribution of the selenium-chelating pea oligopeptide in Example 1 was shown in FIG. 2.

Figure 2:
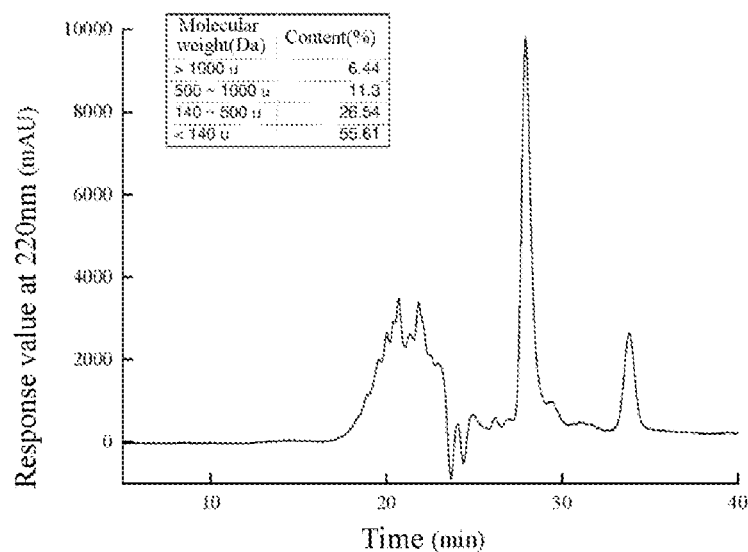
FIG. 2 is a gel chromatogram of molecular weight distribution of selenium-chelating pea oligopeptide in Example 1 of the present disclosure.

According to Table 2 and FIG. 2, it can be seen that more than 85% of the molecular weight distribution was below 1000 u, small peptides of <500 u have the highest content, accounting for more than 68%, such small peptides are easier to function in organisms.

TABLE 2

Molecular weight distribution of selenium-chelating pea oligopeptide chelate

| | Molecular weight distribution % | | | | |
|---|---|---|---|---|---|
| | >1000 u | 500-1000 u | 140-500 u | <140 u | Total of below 1000 u |
| Example 1 | 6.44 | 11.30 | 26.54 | 55.61 | 93.56 |
| Example 2 | 5.42 | 16.58 | 27.45 | 49.33 | 94.58 |
| Example 3 | 5.05 | 18.37 | 27.99 | 48.34 | 94.71 |
| Example 4 | 4.92 | 18.81 | 24.80 | 44.04 | 87.65 |

Taking the selenium-chelating pea oligopeptide prepared in Example 1 as a sample, the following tests, characterization and evaluation were performed, including:
1. UV Full-Wavelength Scanning 0.05 g/mL of pea oligopeptide aqueous solution and selenium-chelating pea oligopeptide aqueous solution were respectively prepared to perform UV full-wavelength scanning, and the scanning wavelength range was 200-600 nm. The results were shown in FIG. 3.

Figure 3:
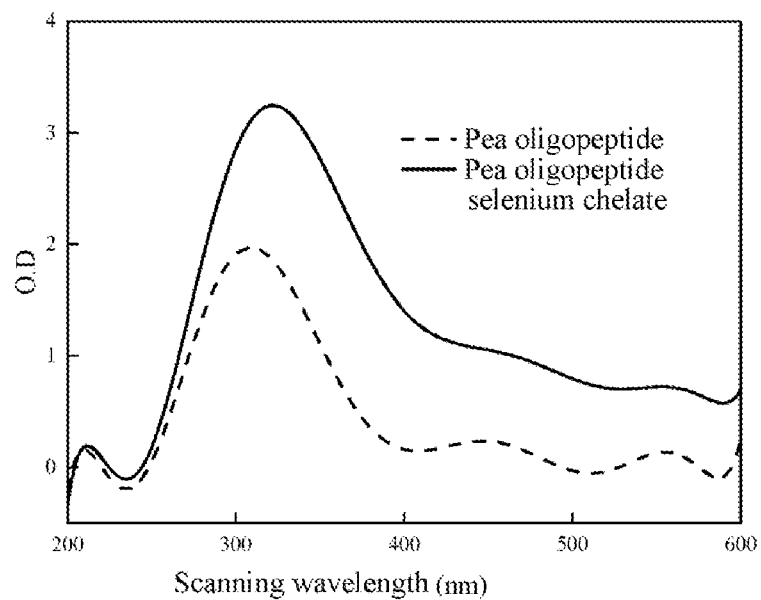
FIG. 3 is UV full-wavelength scanning diagrams of pea oligopeptide and selenium-chelating pea oligopeptide in Example 1 of the present disclosure.

As shown in FIG. 3, the pea oligopeptide had a maximum absorption peak at 309 nm, and when the pea oligopeptide reacted with the sodium selenite to form the selenium-chelating pea oligopeptide, the maximum absorption peak was red-shifted to 322 nm, and the O.D value of the maximum absorption peak also increased. This proved that the material structure of the pea oligopeptide had changed, selenium and the peptide were combined to form a structure with stronger light absorption performance, which is a result of the change in degree of valence electron transition after the reaction of the pea oligopeptide with the selenium.

2. Scanning Electron Microscope Photograph

Figure 4:
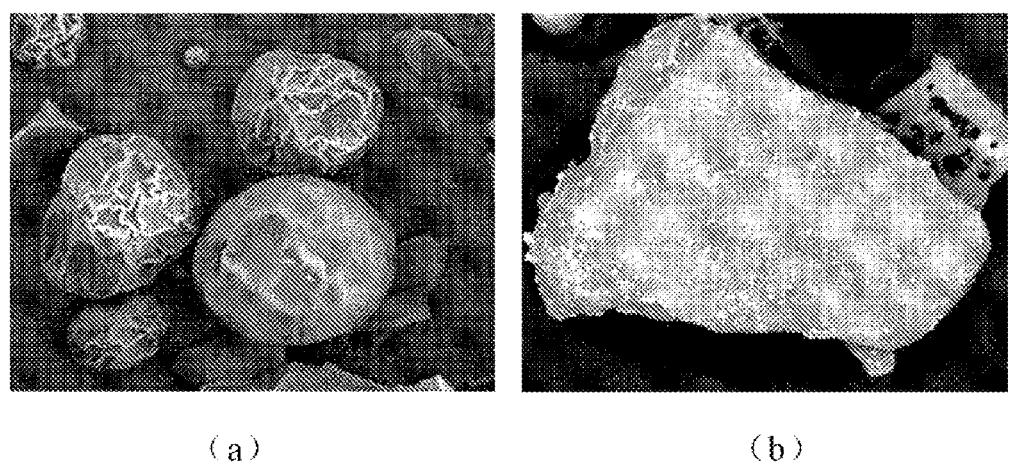
FIG. 4 is scanning electron micrographs (×1000) of pea oligopeptide and selenium-chelating pea oligopeptide in Example 1 of the present disclosure.

FIG. 4(a) and FIG. 4(b) were scanning electron microscope photograph of the pea oligopeptide and the selenium-chelating pea oligopeptide, respectively. As shown in FIG. 4(a), before reaction, the pea oligopeptide were obviously spherical particles, and at 1000 times magnification, it can be seen that there were wrinkles on surfaces of pea oligopeptide particles, and the particle sizes of the whole particles were less than 50 µm. As shown in FIG. 4(b), after the reaction, the particles of the selenium-chelating pea oligopeptide changed greatly in shape and lost their spherical shape. The largest particle size was more than 300 µm. The wrinkles on the surfaces of the selenium-chelating pea oligopeptide were mostly stretched and there were holes. The change of the particles was obvious, which proved that the particles before and after reaction were two kinds of substances. It was speculated that, after chelation reaction, the surface of the pea oligopeptide was unfolded and the structure was changed to provide sites for binding with selenium.

3. Fourier Infrared Spectroscopy

Figure 5:
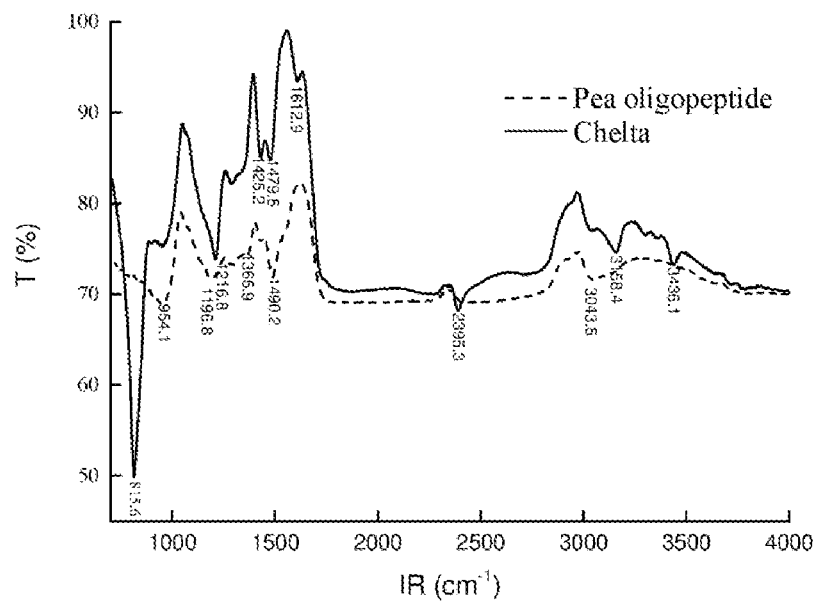
FIG. 5 is infrared spectrograms of pea oligopeptide and selenium-chelating pea oligopeptide in Example 1 of the present disclosure.

As shown in FIG. 5, in comparison of absorption peaks of the pea oligopeptide and the selenium-chelating pea oligopeptide (chelta), the shape of the peaks had changed. Specifically, the pea oligopeptide had absorption peaks near 3040 $cm^{-1}$ and 954 $cm^{-1}$, indicating the presence of —COOH; and the absorption peak near 3040 $cm^{-1}$ of the selenium-chelating pea oligopeptide became narrow, and the absorption peak near 954 $cm^{-1}$ became very weak, indicating that free carboxyl group was absent, and the carboxyl group may coordinate with selenium in the form of covalent bond. The selenium-chelating pea oligopeptide has double peaks near 3158 $cm^{-1}$ and 3436 $cm^{-1}$, and peak near 1216 $cm^{-1}$, indicating that —$NH_2$ wa present and —$NH_2$ was free.

Theoretically, the chelation mechanism of selenium-chelating pea oligopeptide is coordination of $Se^{4+}$ and —$NH_2$, and the carboxyl group also forms coordination with $Se^{4+}$ in the form of covalent bond. It was speculated that, in the selenium-chelating pea oligopeptide chelate, $Se^{-1}$ provided a 4d empty orbital, O and N can provide a lone pair of electrons, which can respectively occupy an empty orbital to form a coordination bond. This speculation was also consistent with other related studies. For details, please refer to the literature Fei GAO, Weiyou WANG, Jun LU, etc., Preparation and Infrared Spectroscopic Characterization of Marine Fish Bone Collagen Peptide-Calcium Chelate [J]. *Journal of Ocean University of China* (Natural Science), 2015, 45 (1): 47-54 and the literature Shasha SONG, Fei GAO, Difeng REN, etc., Preparation and Infrared Spectroscopic Identification of Black-bone Chicken Peptide-Iron Chelate [J]. *Food and Fermentation Industries*, 2013, 39 (6): 13-17.

4. Thermal Stability of Selenium-Chelating Pea Oligopeptide

After the selenium-chelating pea oligopeptide was treated at 40, 60, 80 and 100° C. for 2 hours, its molecular weight distribution was shown in Table 3. It can be seen from Table 3 that, after heat treatment, in the selenium-chelating pea oligopeptide, a proportion of components with molecular weight less than 1000 u fluctuated around 93%, and a variation range of a proportion of components with molecular weight more than 1000 u was less than 2%.

TABLE 3

Molecular weight distribution of selenium-chelating pea oligopeptide after treated at different temperatures

| Temperature/ ° C. | Molecular weight distribution/% | | | | Total (below 1000 u) |
|---|---|---|---|---|---|
| | >1000 u | 500-1000 u | 140-500 u | <140 u | |
| Control | 6.435 | 11.301 | 26.538 | 55.613 | 93.452 |
| 40 | 6.685 | 15.117 | 24.528 | 53.172 | 92.817 |
| 60 | 4.666 | 18.138 | 27.080 | 49.496 | 94.714 |
| 80 | 5.189 | 18.009 | 28.021 | 48.074 | 94.104 |
| 100 | 6.099 | 18.276 | 28.976 | 46.096 | 93.347 |

Figure 6:
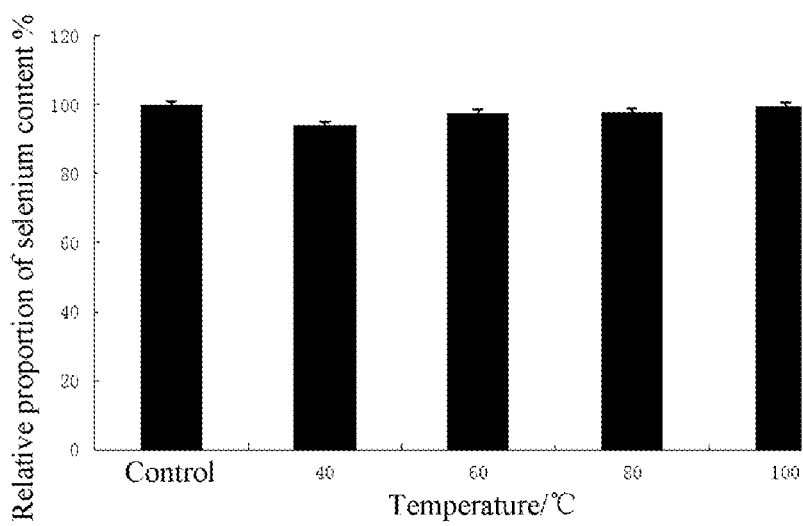
FIG. 6 shows selenium content in selenium-chelating pea oligopeptide after treated in different temperature conditions in Example 1 of the present disclosure.

On the whole, the influence of temperature increased the proportion of 140-1000 u. After treated at different temperatures, the selenium content of the selenium-chelating pea oligopeptide was shown in FIG. 6. Compared with the control, there was no significant difference in the selenium content of the selenium-chelating pea oligopeptide after treated at different temperatures (a=0.05), indicating that the selenium-chelating pea oligopeptide had good thermal stability. It was speculated that, this may be due to the fact that the pea oligopeptide only had the primary structure of protein, and had a strong tolerance to temperature.

5. Acid-Alkali Stability of Selenium-Chelating Pea Oligopeptide

After the selenium-chelating pea oligopeptide chelate was treated under different pH conditions, its molecular weight distribution was shown in Table 4. Under neutral conditions, the proportion of molecular weight less than 140 u increased by about 10%, with the greatest change in the same column. It may be that such small peptides (especially those with molecular weight of less than 500 u) were resistant to an acid-alkali environment, but were easy to break under a neutral condition. The proportion of molecular weight less than 1000 u was not greatly changed, with the maximum change rate not exceeding 3%, which can further prove that the peptide chain was resistant to the acid-alkali environment.

TABLE 4

Molecular weight distribution of selenium-chelating pea oligopeptide after treated at different pH

| pH value | Molecular weight distribution/% | | | | Total of below 1000 u |
|---|---|---|---|---|---|
| | >1000 u | 500-1000 u | 140-500 u | <140 u | |
| Control | 5.004 | 18.394 | 28.008 | 48.353 | 94.755 |
| 3 | 3.580 | 19.124 | 27.256 | 49.623 | 96.004 |
| 5 | 4.924 | 20.024 | 27.186 | 47.312 | 94.522 |
| 7 | 5.387 | 14.522 | 21.321 | 58.175 | 94.018 |
| 9 | 8.073 | 16.106 | 24.721 | 50.998 | 91.826 |
| 11 | 4.693 | 19.440 | 27.372 | 48.141 | 94.952 |

Figure 7:
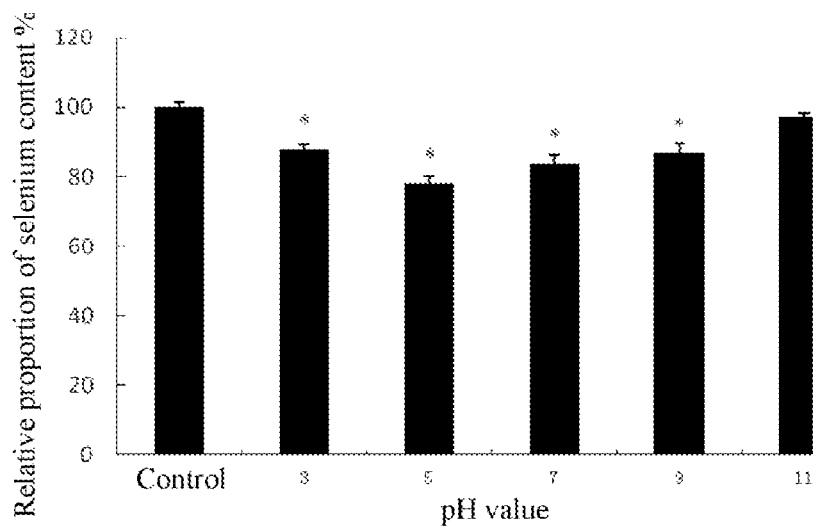
FIG. 7 shows selenium content in selenium-chelating pea oligopeptide after treated in different acid-alkali conditions in Example 1 of the present disclosure.

FIG. 7 showed the change of the selenium content after treatment at different pH. In slightly acidic and neutral environments, the selenium content was significantly reduced (a=0.05), with the change rate being about 20%. In an alkaline environment, the selenium content had a small change. But in the pH range of 3-11, the selenium content was still above 78%, indicating that the product of the pea oligopeptide chelated with the selenium still had a strong stability to the acid-alkali environment.

6. In Vitro Digestion Stability of Selenium-Chelating Pea Oligopeptide

The selenium-chelating pea oligopeptide was treated with pepsin, trypsin, pepsin followed by the trypsin, respectively, and the molecular weight distribution results were shown in Table 5. It can be seen from Table 5 that, after the selenium-chelating pea oligopeptide was treated by different in vitro digestion methods, the proportion of molecular weight less than 1000 u increased, where the proportion after pepsin treatment increased by about 7%, the proportion after trypsin treatment increased by about 9%, and the proportion after pepsin treatment followed by trypsin treatment increased by about 12%. This showed that the pea oligopeptide was digested by enzyme and decomposed into peptide segments with smaller molecular weight. After enzymolysis, the proportion of molecular weight less than 1000 u was more than 90%. Small peptide segments, especially dipeptides and tripeptides were more conducive to absorption by the human body.

Figure 8:
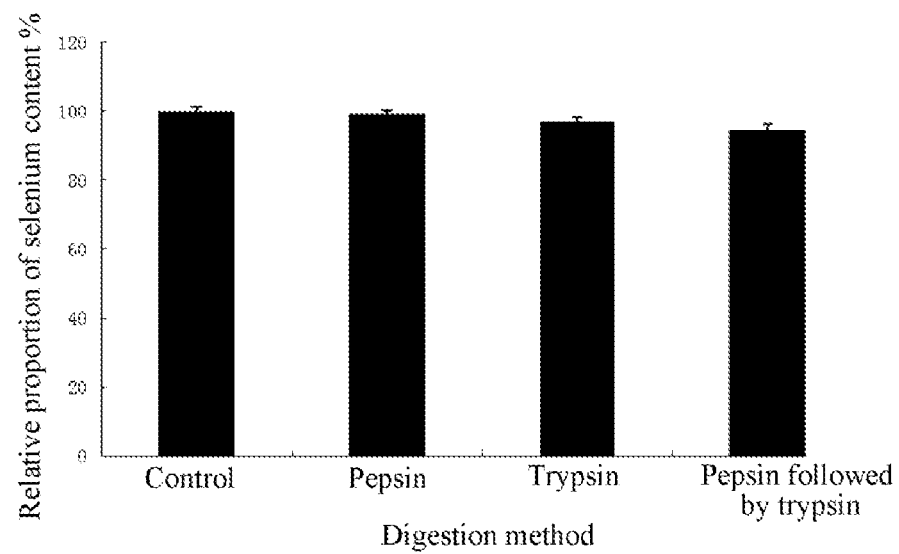
FIG. 8 shows selenium content in selenium-chelating pea oligopeptide after treated in different digestion ways in Example 1 of the present disclosure.

As shown in FIG. 8, after treatments in different digestion methods, the selenium content in the selenium-chelating pea oligopeptide had a small change, with a change of less than 3% compared with the selenium content before digestion treatments. Combined with a change table of molecular weight distribution, after the selenium-chelating pea oligopeptide was digested by enzyme, although it was hydrolyzed into small peptide segments, the coordination structure of the selenium and the peptide was not completely destroyed; it can be inferred that the coordination bond between the pea oligopeptide and the selenium was relatively stable and would not be damaged by the break of the peptide chain. Thus, the selenium can stably pass through gastric juice and intestinal juice along with small peptide segments, and was finally absorbed indirectly in the intestinal tract through the absorption of the peptide by small intestinal mucosa.

TABLE 5

Molecular weight distribution of selenium-chelating pea oligopeptide in different digestion methods

| Digestion method | Molecular weight distribution/% | | | | Total (below 1000 u) |
| --- | --- | --- | --- | --- | --- |
| | >1000 u | 500-1000 u | 140-500 u | <140 u | |
| Control | 4.867 | 18.829 | 24.809 | 44.057 | 87.695 |
| Pepsin | 4.811 | 13.912 | 35.075 | 45.780 | 94.766 |
| Trypsin | 3.014 | 11.727 | 37.916 | 46.853 | 96.496 |
| Pepsin followed by trypsin | 1.147 | 9.537 | 40.394 | 48.811 | 98.742 |

Figure 9:
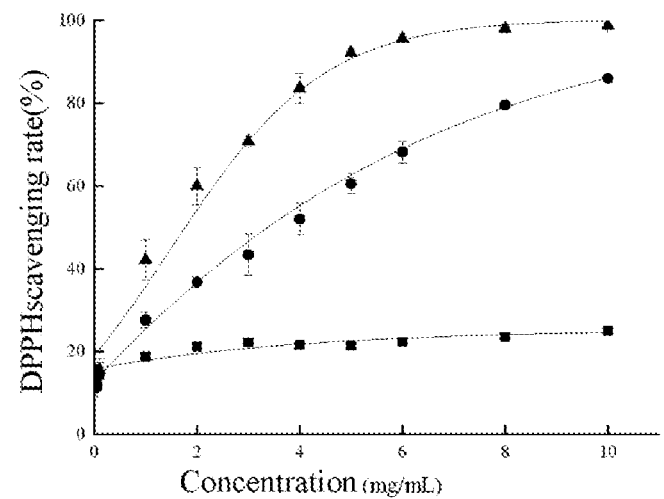
FIG. 9 is a comparison diagram of scavenging DPPH free radicals by selenium-chelating pea oligopeptide and its synthetic raw materials in Example 1 of the present disclosure.

7. Scavenging of DPPH Free Radical by Selenium-Chelating Pea Oligopeptide Chelate In FIG. 9, ■, ●, ▲ represent sodium selenite, pea oligopeptide and selenium-chelating pea oligopeptide, respectively. As shown in FIG. 9, the sodium selenite had a very weak scavenging capacity for DPPH free radical, and had nothing to do with the concentration of sodium selenite, and its scavenging rate was almost stable at about 20%.

The pea oligopeptide had the scavenging capacity for DPPH free radical, and the scavenging rate increased with the increase of the concentration of the pea oligopeptide, showing a parabolic trend, and had gradually decreasing change of scavenging rate; based on a parabolic formula, $IC_{50}$ value of pea oligopeptide scavenging DPPH free radical was calculated to be 3.39±0.02 mg/mL.

The selenium-chelating pea oligopeptide had a relatively strong scavenging capacity for DPPH free radical, which changed with the change of dose of chelate. As the concentration of the chelate increased, the scavenging rate of the chelate for DPPH free radical was also gradually increased; in a range where the concentration of the chelate was lower than 5 mg/mL, a change trend of the scavenging rate was almost linear; as the concentration continued to increase, the change of the scavenging rate gradually slowed down, showing a parabolic trend.

Figure 10:
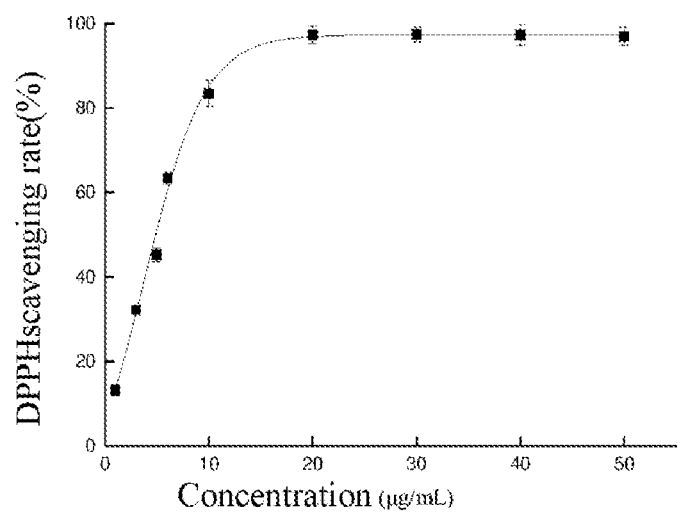
FIG. 10 is a comparative diagram of VC scavenging DPPH free radicals.

After calculation, the $IC_{50}$ of selenium-chelating pea oligopeptide was 1.77±0.01. After chelation, the scavenging capacity of the chelate on DPPH free radicals became strong, and was higher than that of the pea oligopeptide and the sodium selenite as raw materials, and the $IC_{50}$ value of the chelate was almost half of that of the pea oligopeptide. Based on FIG. 10, $IC_{50}$ value of ascorbic acid as a positive control was calculated to be 4.85±0.02 μg/mL.

8. Scavenging of OH Free Radical by Selenium-Chelating Pea Oligopeptide Chelate

Figure 11:
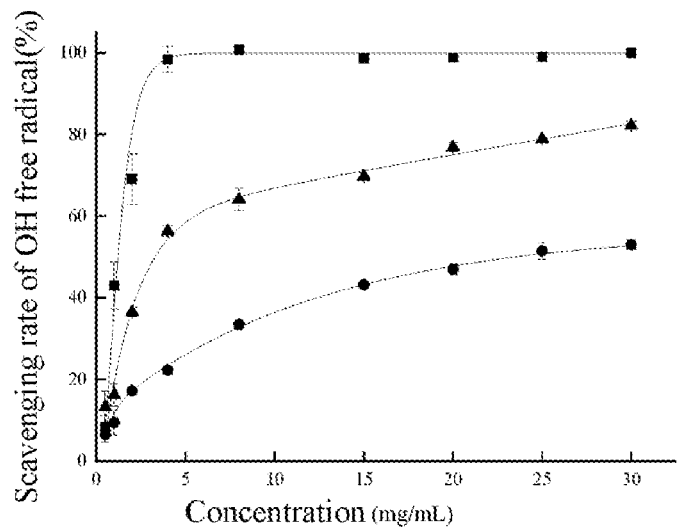
FIG. 11 is a comparison diagram of scavenging OH free radicals by selenium-chelating pea oligopeptide and its synthetic raw materials in Example 1 of the present disclosure.

In FIG. 11, ■, ●, ▲ represent sodium selenite, pea oligopeptide and selenium-chelating pea oligopeptide, respectively. As shown in FIG. 11, as the concentration of sodium selenite increased, its scavenging capacity on OH free radical changed almost linearly with a large slope. When the concentration of sodium selenite was 5 mg/mL, its scavenging rate for OH free radical can reach 100%. Based on a fitted curve formula, $IC_{50}$ value of sodium selenite scavenging OH free radicals was calculated to be 1.23+0.02 mg/mL.

The pea oligopeptide had a certain scavenging capacity for OH free radical, and, with the increase of concentration of pea peptide, the scavenging rate showed a change trend of parabola. Based on a fitted parabolic curve equation, $IC_{50}$ value of pea oligopeptide scavenging OH free radical was calculated to be 23.55+0.07 mg/mL.

Figure 12:
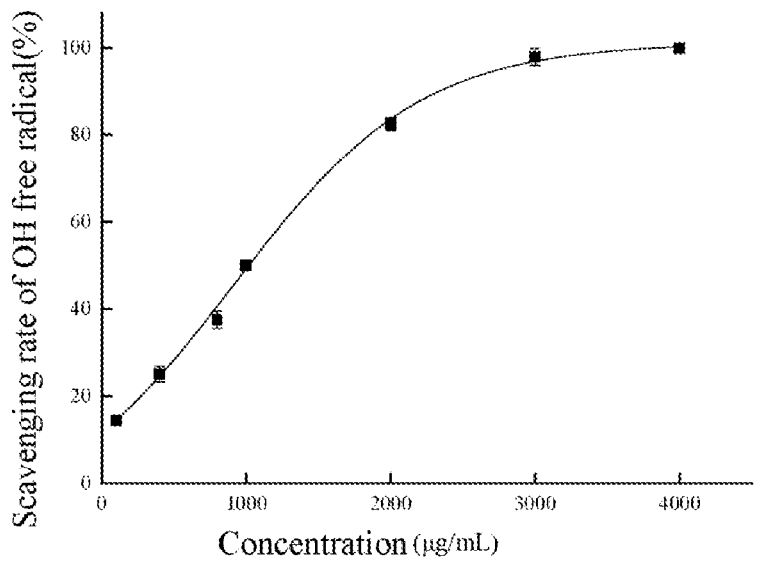
FIG. 12 is a comparative diagram of VC scavenging OH free radicals.

The selenium-chelating pea oligopeptide had a relatively strong scavenging capacity for OH free radical, and it can be seen from FIG. 11 that in a range where its concentration was lower than 5 mg/mL, the change curve of the scavenging rate with concentration was close to be linear, with a large slope; as the concentration continued to increase, the change trend of the scavenging curve slowed down, and the slope decreased, and almost had the same change slope as the pea oligopeptide. It was speculated that, in a range where the concentration was lower than 5 mg/mL, the scavenging capacity of the selenium-chelating pea oligopeptide on OH free radical was greatly affected by the concentration of sodium selenite; beyond this range, the scavenging capacity of the sodium selenite on OH free radical was saturated, and the scavenging capacity of the selenium-chelating pea oligopeptide on free radical was mainly affected by the concentration of the pea oligopeptide as raw material. Based on a fitted curve, $IC_{50}$ value of the selenium-chelating pea oligopeptide scavenging OH free radical was calculated to be 3.28±0.04 mg/mL. Based on FIG. 12, $IC_{50}$ value of the ascorbic acid as a positive control to scavenge OH free radical was calculated to be 1024.87±5.96 μg/mL.

9. Reducing Capacity of Selenium-Chelating Pea Oligopeptide

Figure 13:
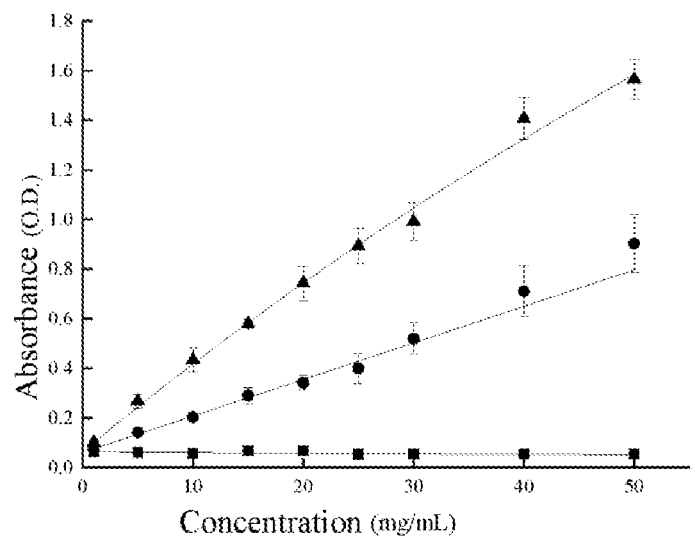
FIG. 13 is a comparison diagram of reducing capacity of selenium-chelating pea oligopeptide and its synthetic raw materials in Example 1 of the present disclosure.

In FIG. 13, ■, ●, ▲ represent sodium selenite, pea oligopeptide and selenium-chelating pea oligopeptide, respectively. As shown in FIG. 13, the sodium selenite had no reducing capacity. The reducing capacity of the pea oligopeptide increased with the increase of its concentration, and the change trend was linear. The reducing capacity of the selenium-chelating pea oligopeptide also increased with the increase of its concentration, and the change trend was also close to be linear, but the reducing capacity of the selenium-chelating pea oligopeptide was higher than that of the pea oligopeptide as raw material.

Figure 14:
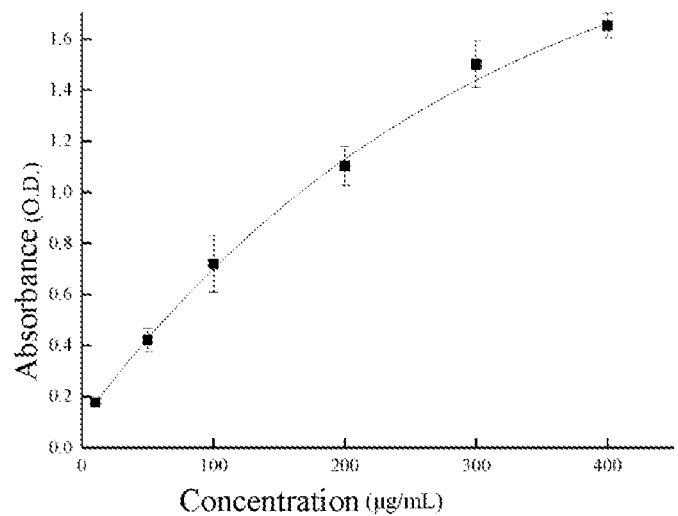
FIG. 14 is a comparative diagram of reducing capacity of VC.
Figure 15:
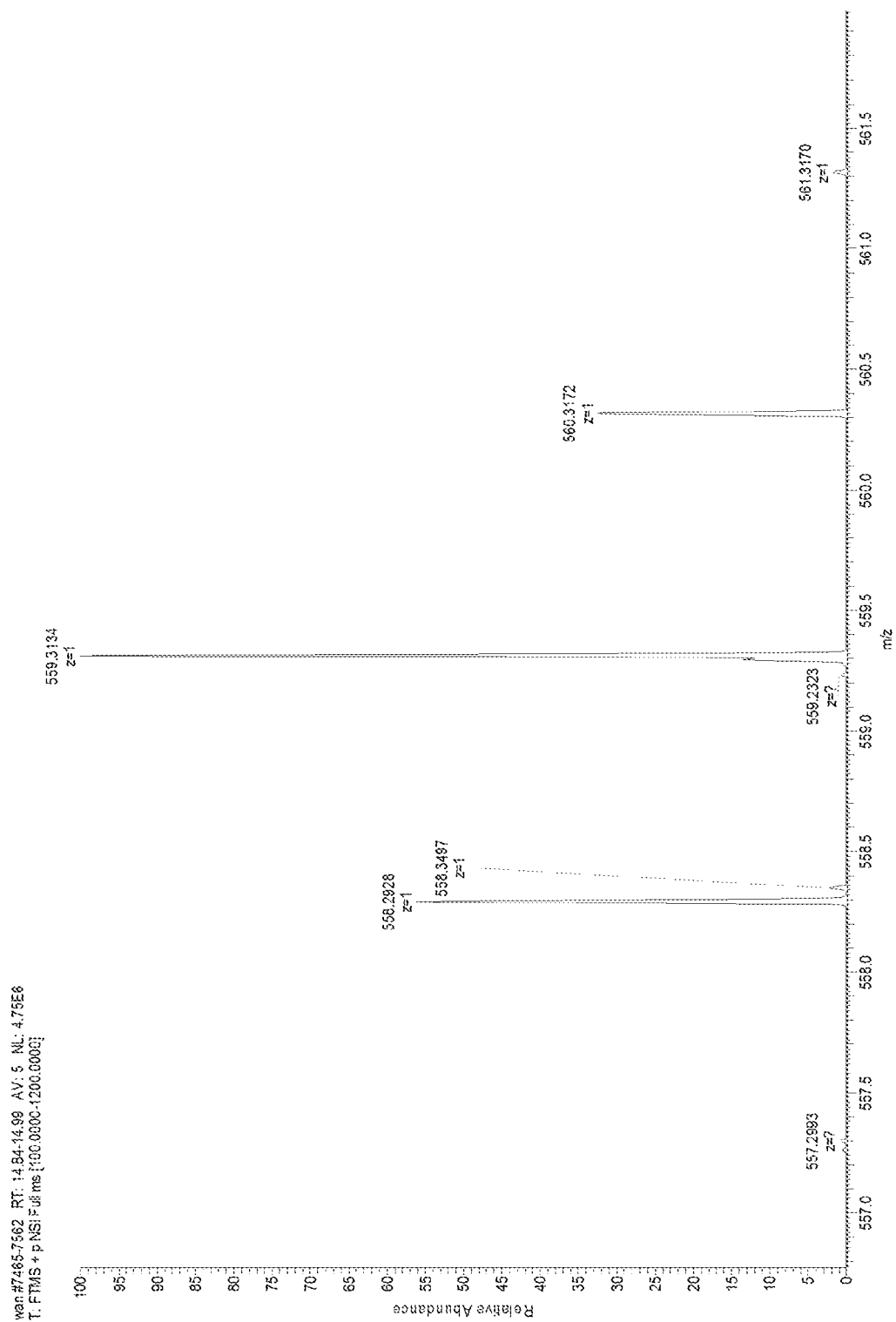
FIG. 15 is a primary mass spectrum of a peptide segment TGRGAP (SEQ ID NO:1)
Figure 16:
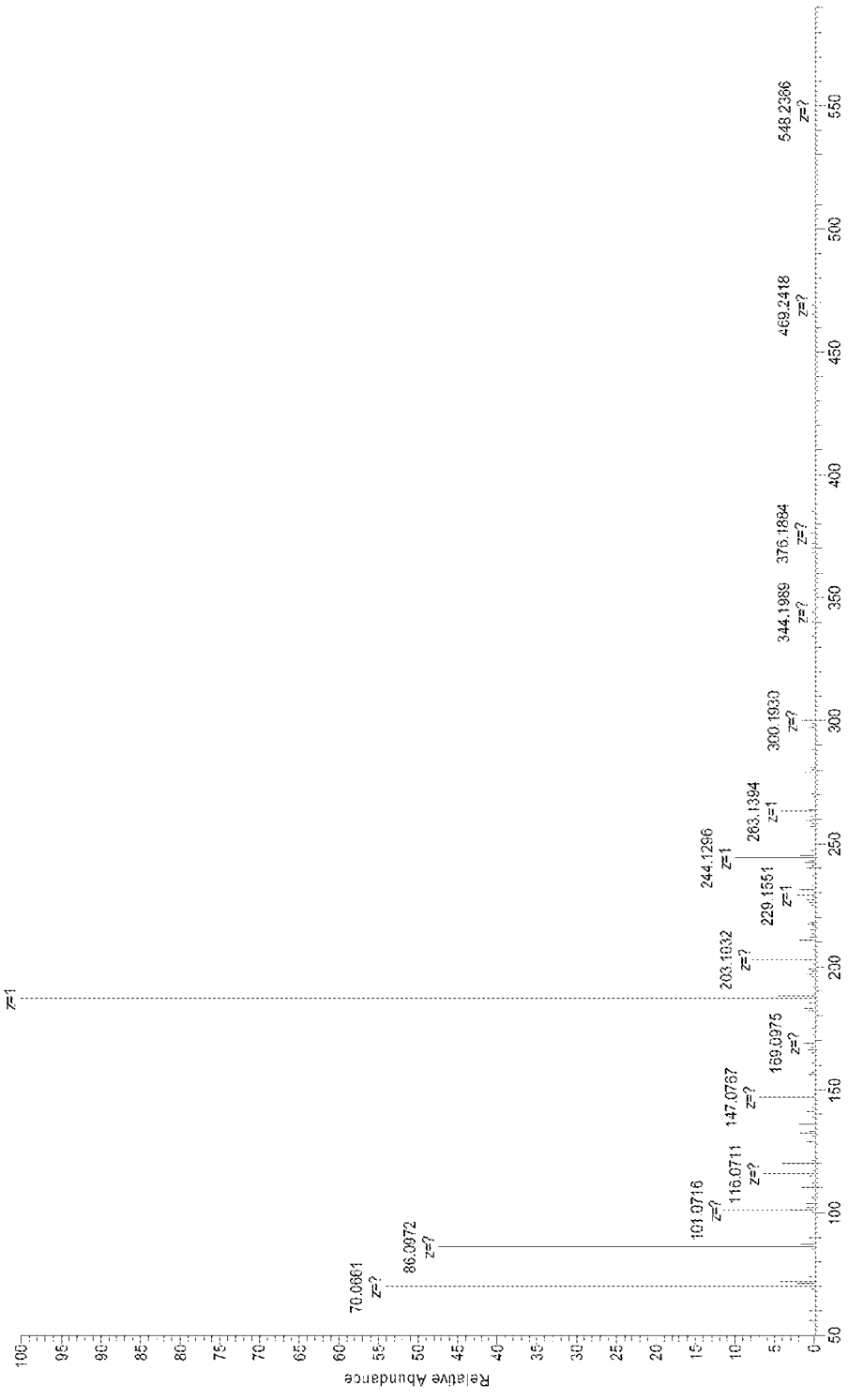
FIG. 16 is a secondary mass spectrum of a peptide segment TGRGAP (SEQ ID NO:1)
Figure 17:
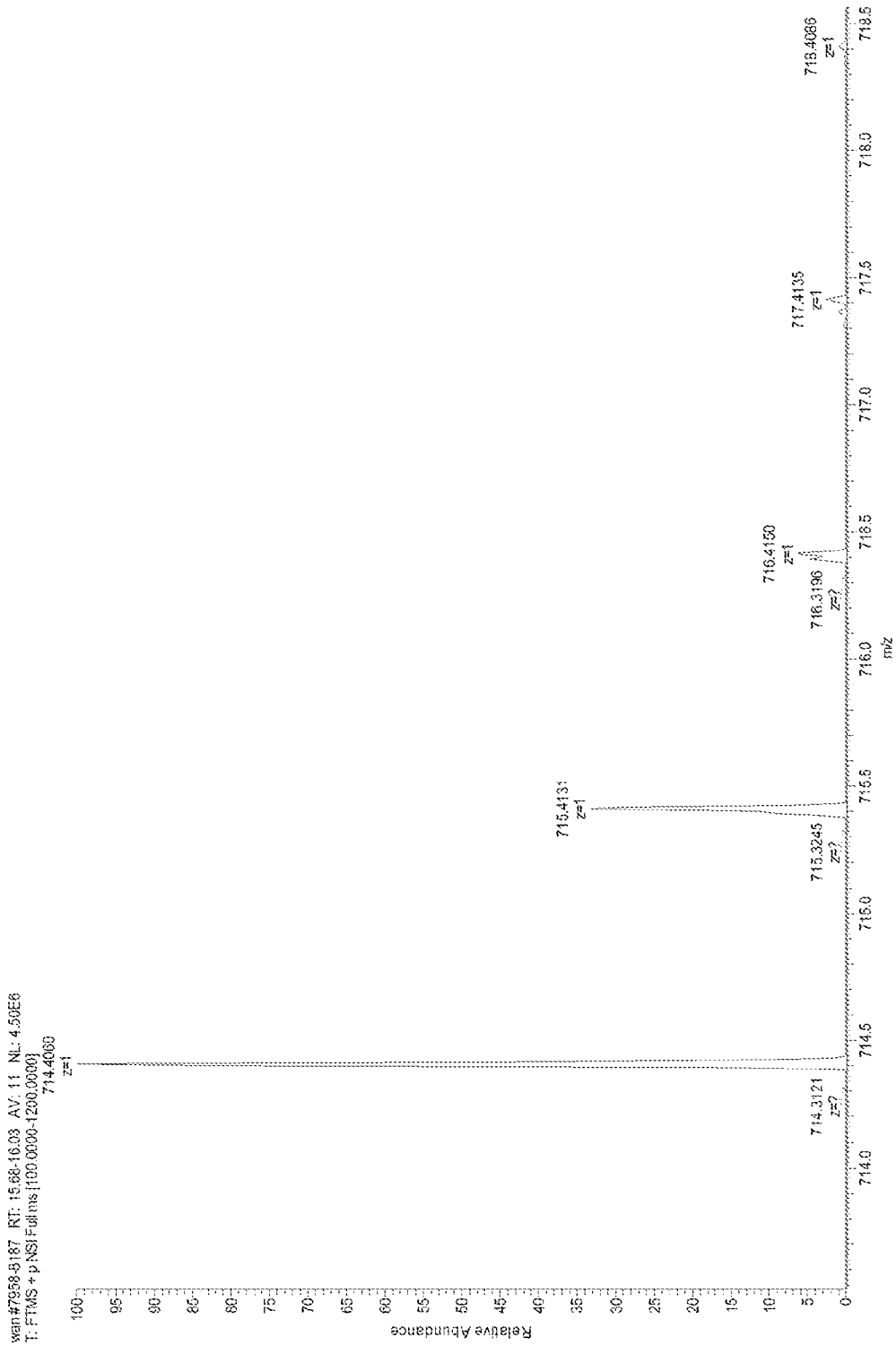
FIG. 17 is a primary mass spectrum of a peptide segment PPKIYP (SEQ ID NO:2)
Figure 18:
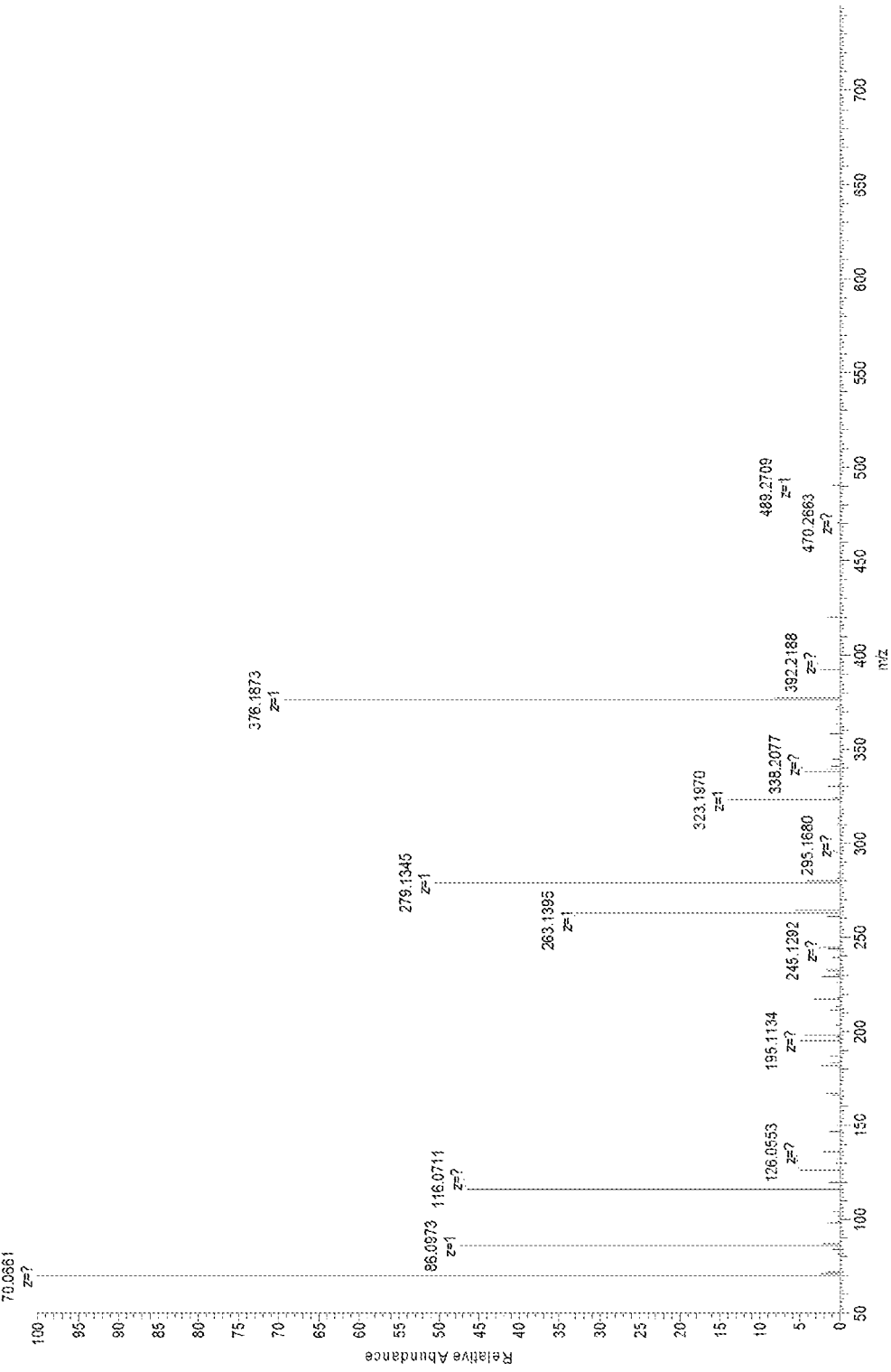
FIG. 18 is a secondary mass spectrum of a peptide segment PPKIYP (SEQ ID NO:2)
Figure 19:
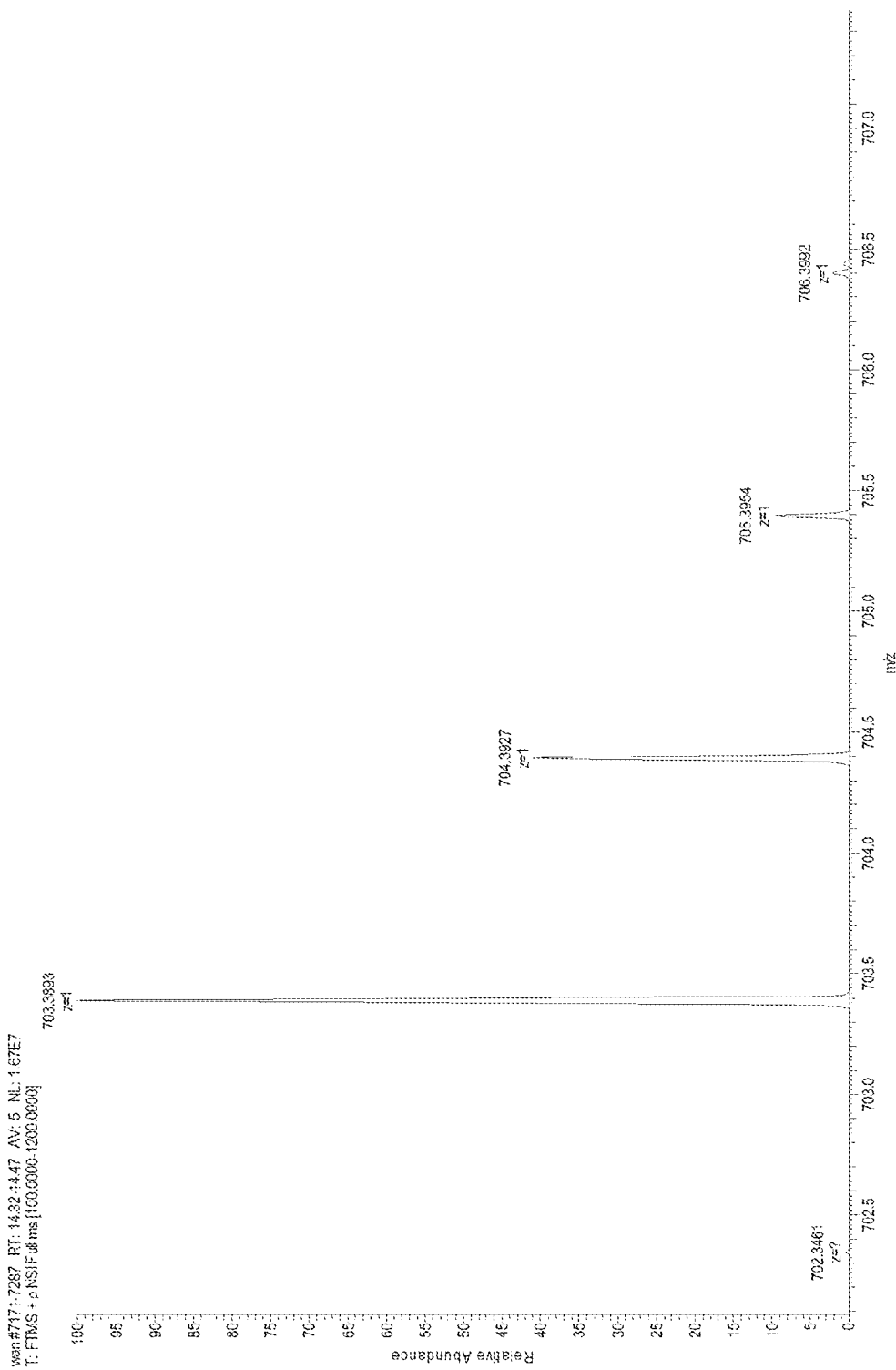
FIG. 19 is a primary mass spectrum of a peptide segment HQMPKP (SEQ ID NO:3)
Figure 20:
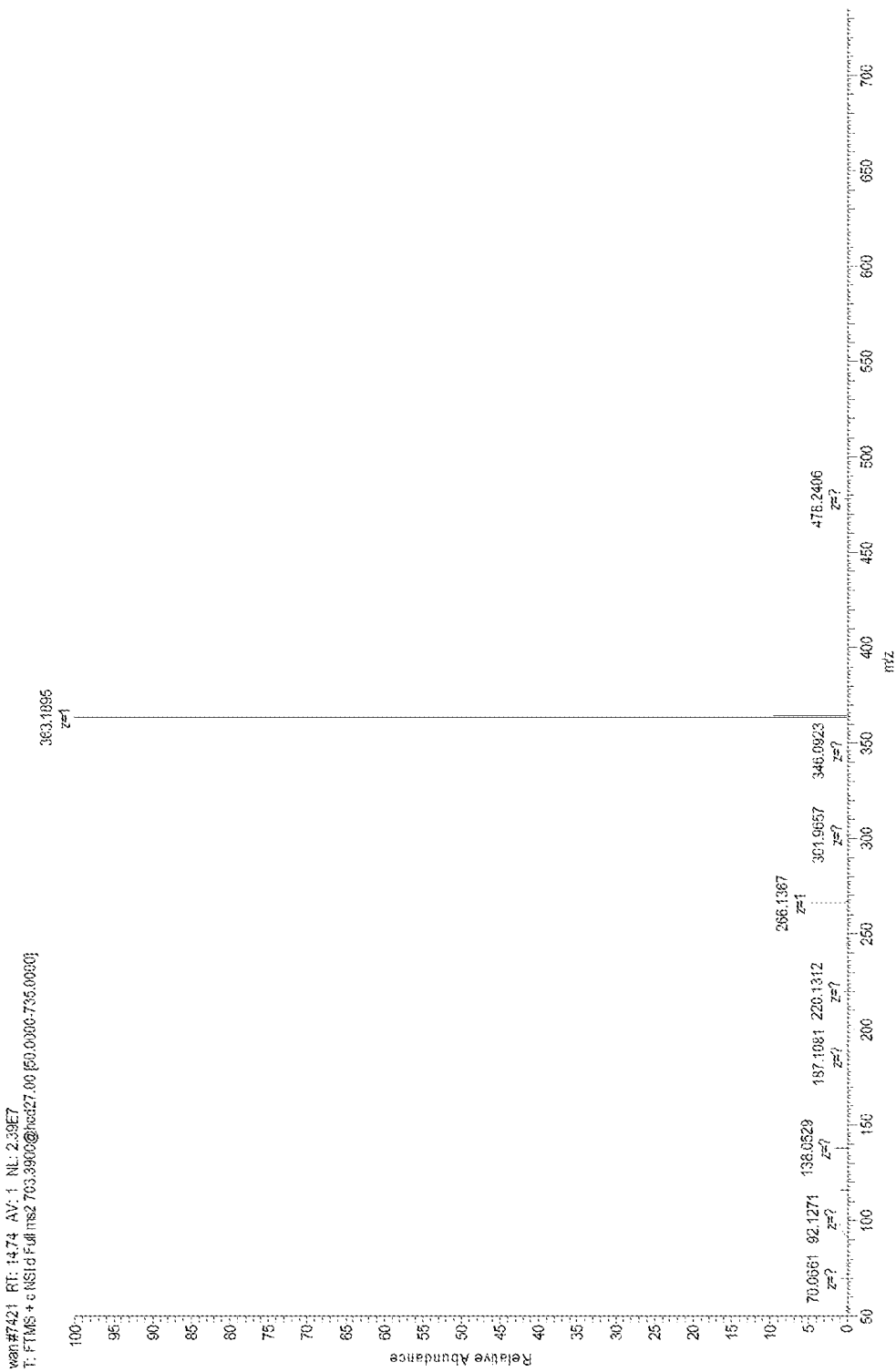
FIG. 20 is a secondary mass spectrum of a peptide segment HQMPKP (SEQ ID NO:3)
Figure 21:
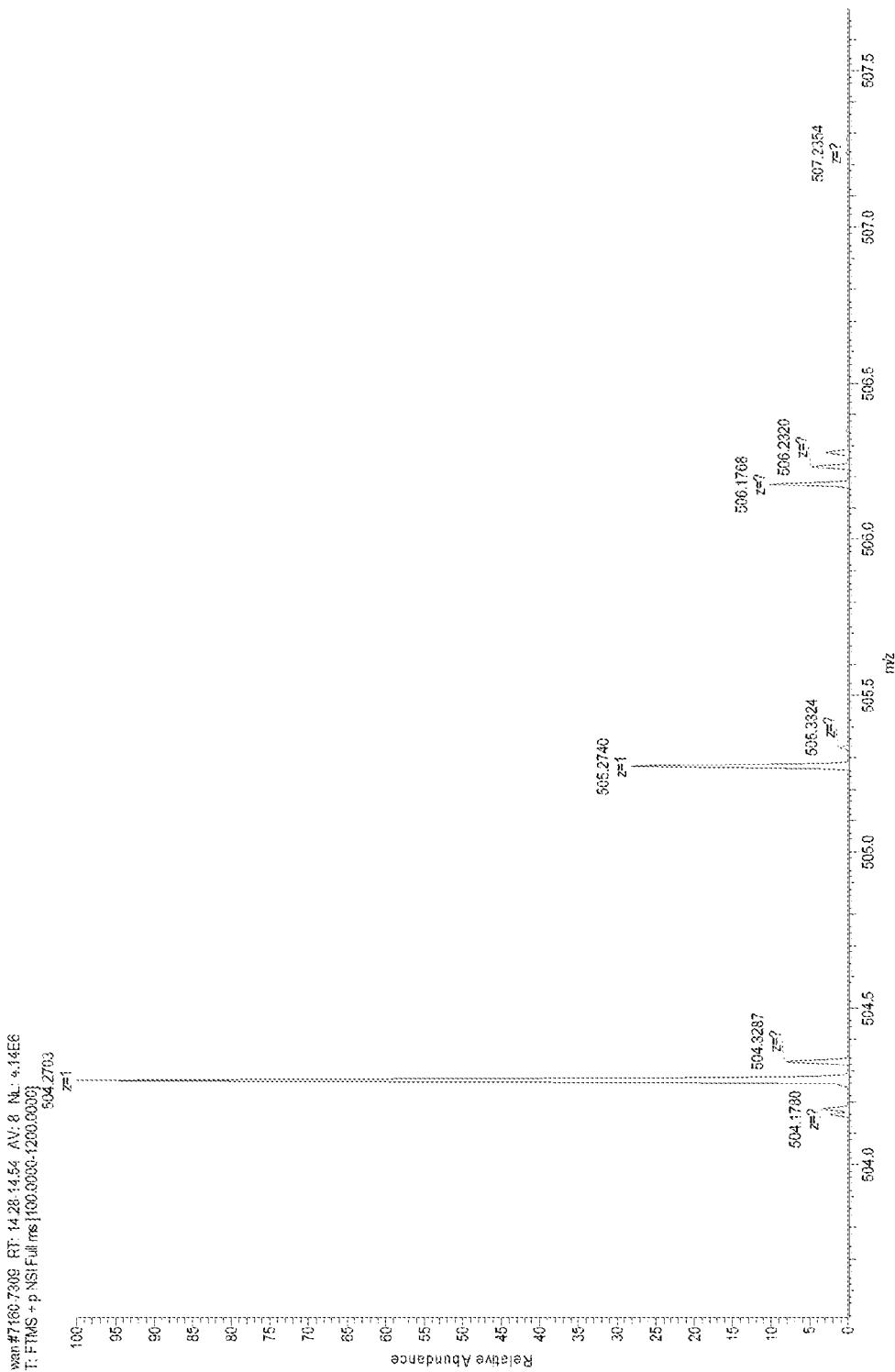
FIG. 21 is a primary mass spectrum of a peptide segment TSSLP (SEQ ID NO: 4)
Figure 22:
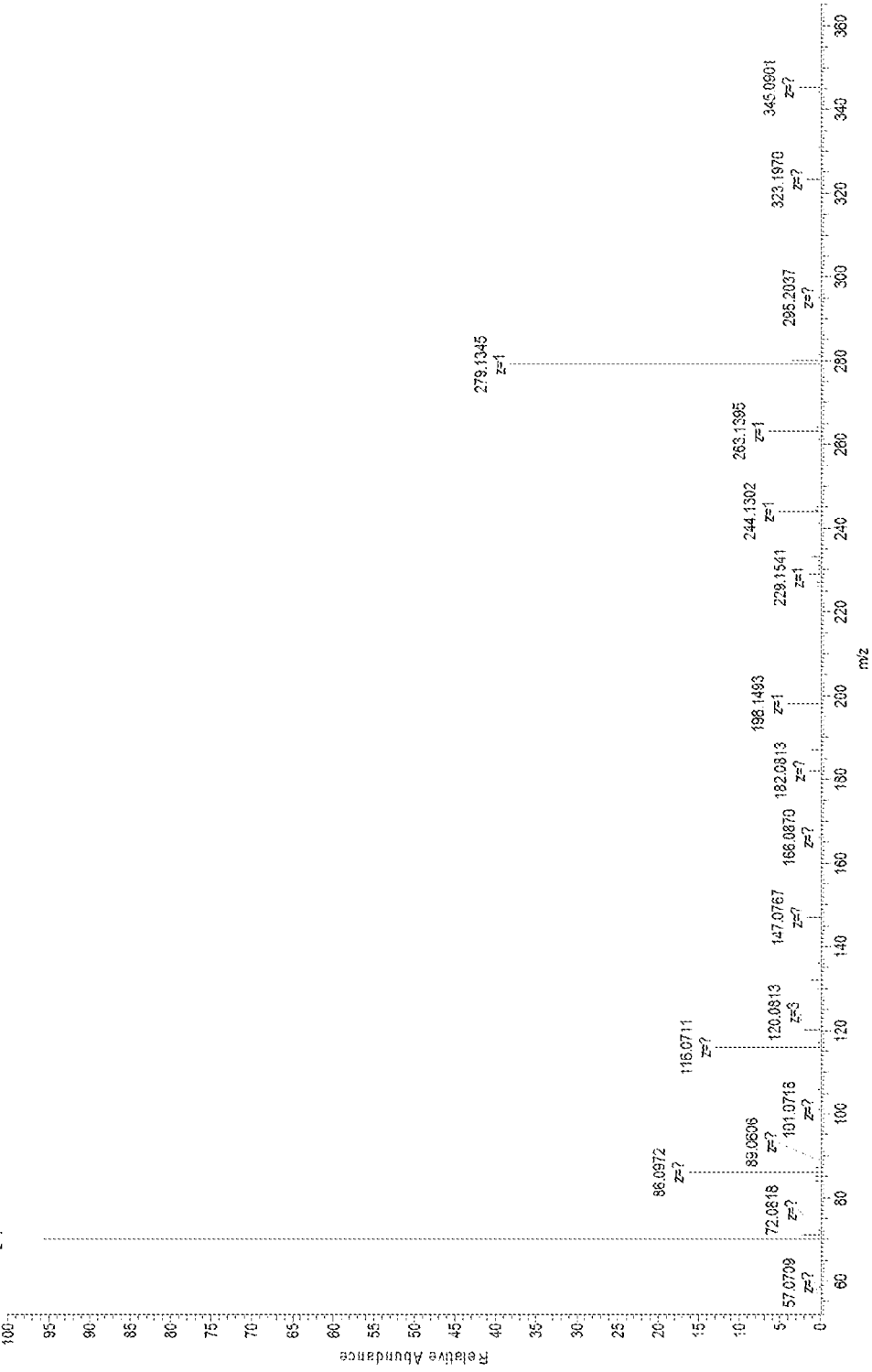
FIG. 22 is a secondary mass spectrum of a peptide segment TSSLP (SEQ ID NO:4)
Figure 23:
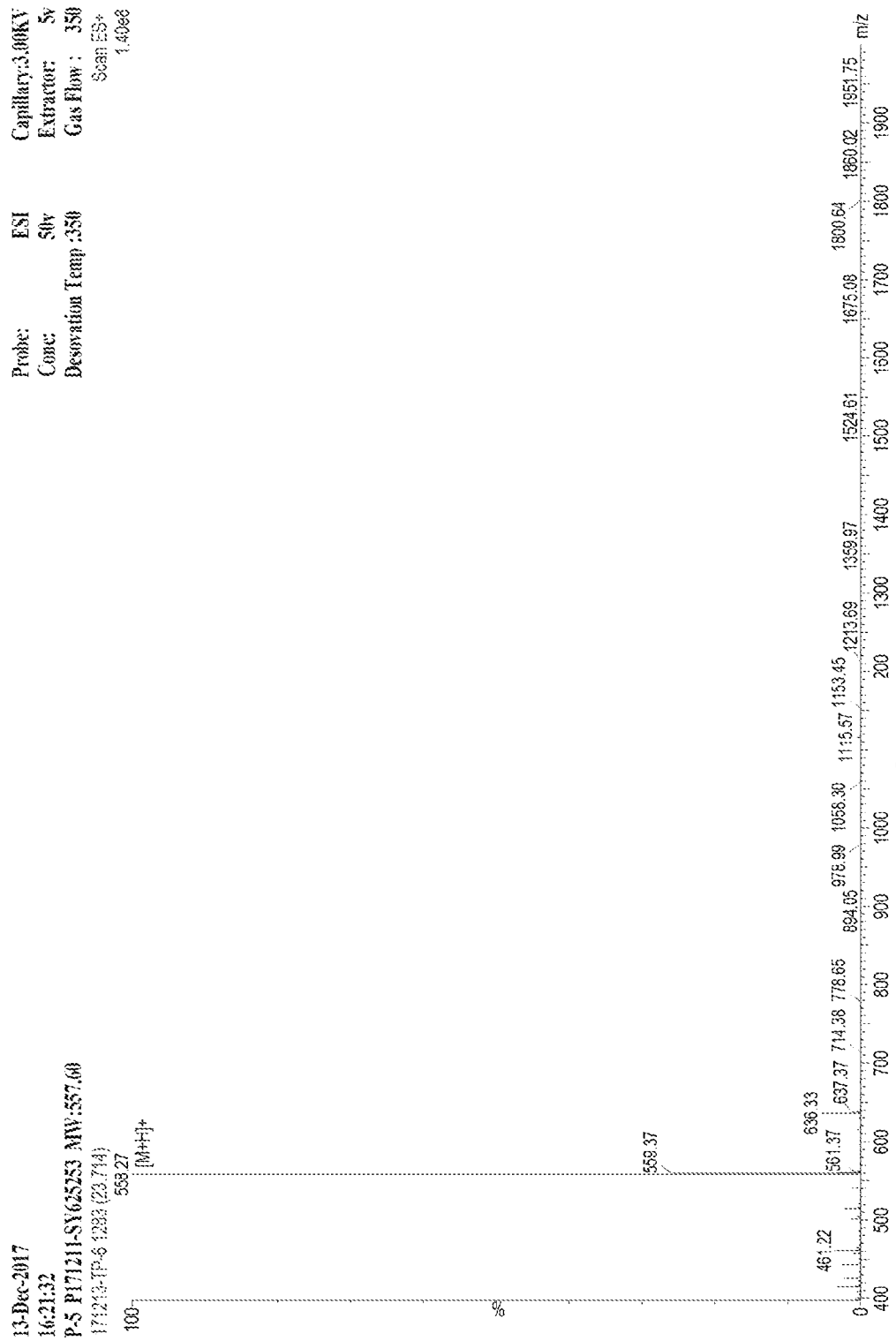
FIG. 23 is a mass spectrum of a synthetic peptide segment TGRGAP (SEQ ID NO:1) standard.
Figure 24:
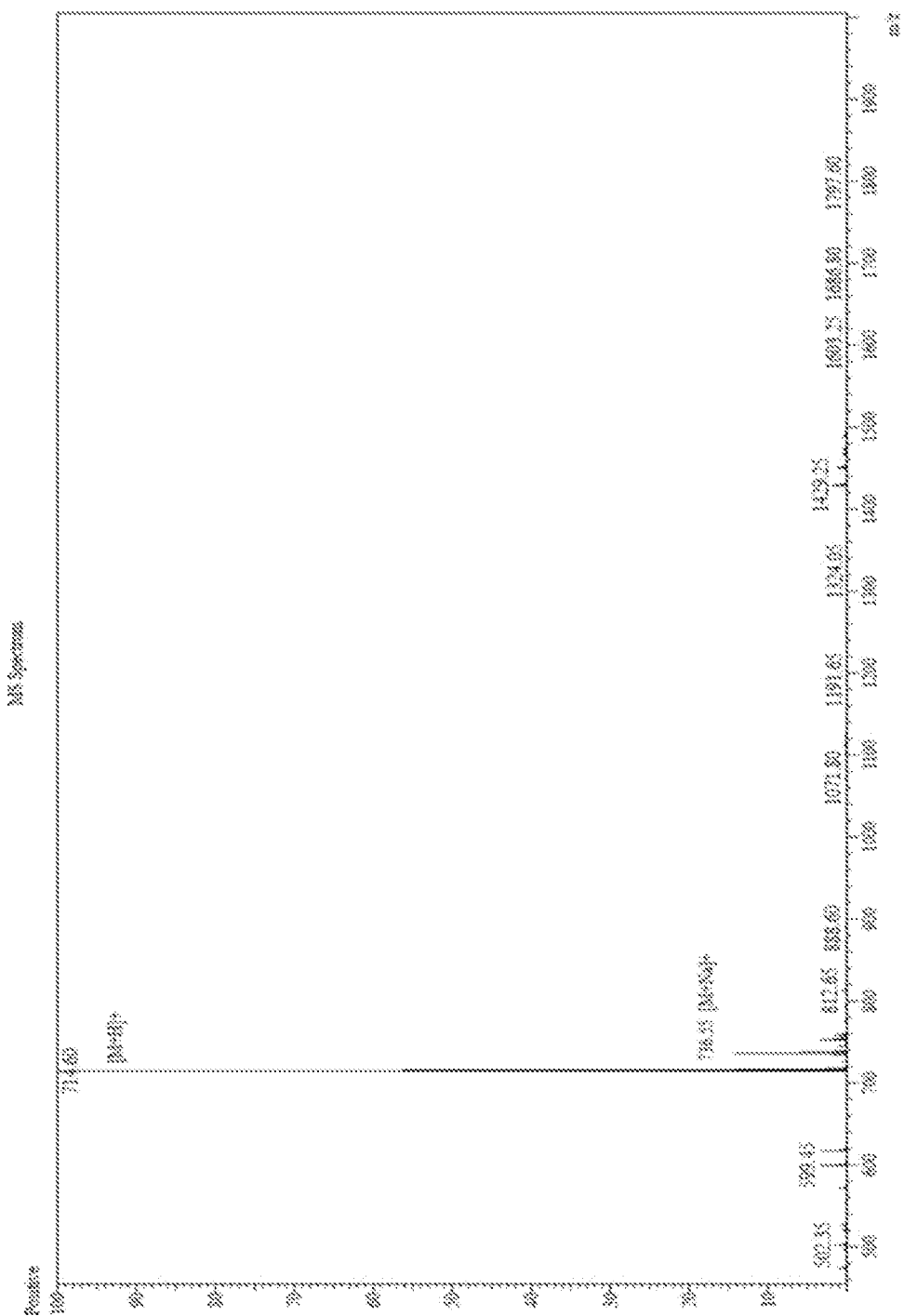
FIG. 24 is a mass spectrum of a synthetic peptide segment PPKIYP (SEQ ID NO:2) standard.
Figure 25:
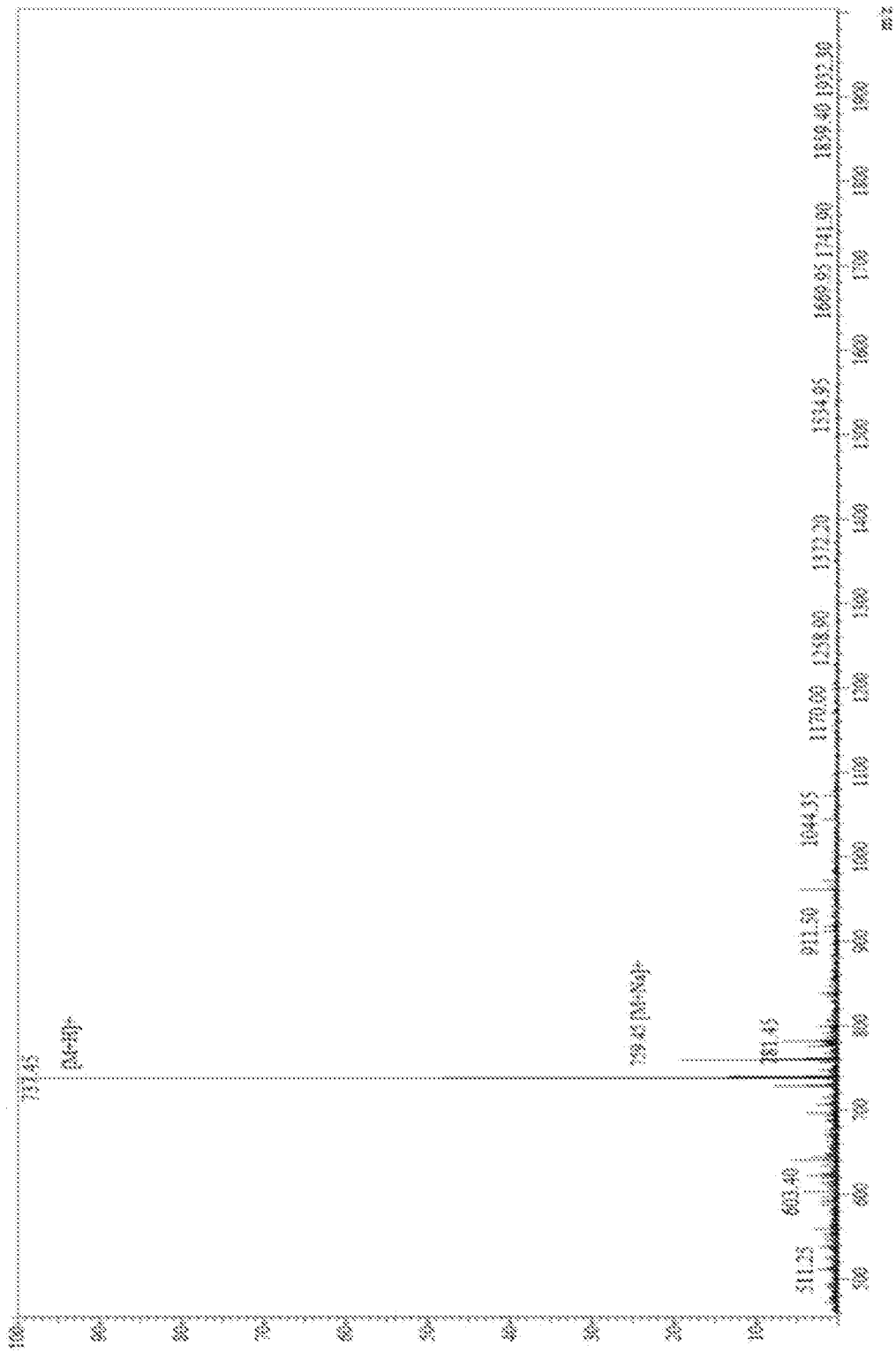
FIG. 25 is a mass spectrum of a synthetic peptide segment HQMPKP (SEQ ID NO:3) standard.
Figure 26:
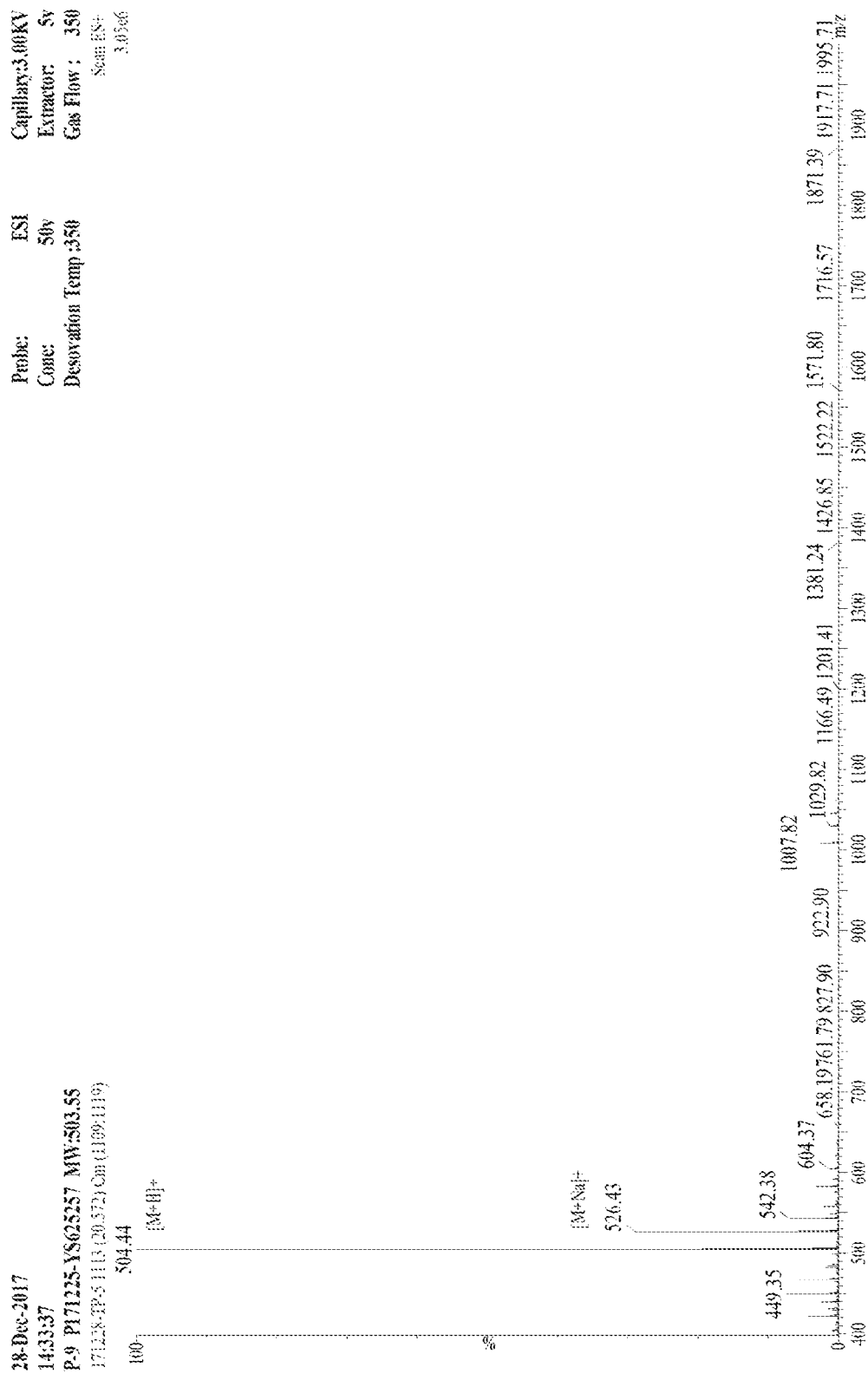
FIG. 26 is a mass spectrum of a synthetic peptide segment TSSLP (SEQ ID NO:4) standard.

As shown in FIG. 14, the reducing capacity of the ascorbic acid as a positive control changed with the change of its concentration, showing a change trend of parabola. In a range where the concentration of the ascorbic acid was lower than 200 μg/mL, the curve changed almost linearly, and as the concentration gradually increased, the change rate of the reducing capacity gradually decreased. When the absorbance value corresponding to the reducing capacity of the ascorbic acid was about 1.6, the required concentration of the ascorbic acid was 400 μg/mL; correspondingly, in order to reach this absorbance, the required concentration of the selenium-chelating pea oligopeptide was 50 mg/mL. When the concentration of the pea oligopeptide was 50 mg/mL, its absorbance value was only about 0.8. It can be inferred from FIG. 13 that the increase of reducing capacity of the selenium-chelating pea oligopeptide was not a simple superposition of reducing capacities of raw material pea oligopeptide and sodium selenite, but the chelating process enhanced the reducing capacity.

10. Peptide Segment Identification and Antioxidant Capacity of Selenium-Chelating Pea Oligopeptide In order to accurately identify possible peptide segments of the selenium-chelating pea oligopeptide, a result identified in database was compared with a result identified in PEAKS search library result to find possible peptide segments. The peptide segments identified in the database and the peptide segments identified by using de novo method were analyzed and aligned, to select 4 credible peptide segments for structure identification by mass spectrometry.

The primary mass spectrum and the secondary mass spectrum of the selected 4 credible peptide segments were shown in FIG. 15 to FIG. 22, the mass spectra of 4 standard synthetic peptide segments were shown in FIG. 23 to FIG. 26, the results of structure identification by mass spectrometry and results of quantitative analysis were shown in Table 6; the identification results of oxidation resistance of standard synthetic peptide segments and the selenium-chelating pea oligopeptide were shown in Table 7.

According to Table 7, it can be known that the selenium-chelating pea oligopeptide had a relatively strong antioxidant capacity. In the 4 peptide segments identified by mass spectrometry, PPKIYP was a peptide segment with relatively strong antioxidant capacity in the selenium-chelating pea oligopeptide.

TABLE 6

Mass spectrometry and content identification results of peptide segments of selenium-chelating pea oligopeptide

| Sequence | Peptide segment | Molecular weight | Content (ng/mg) |
| --- | --- | --- | --- |
| TGRGAP (SEQ ID NO. 1) | Thr-Gly-Arg-Gly-Ala-Pro | 558.29 | 30.00 |
| PPKIYP (SEQ ID NO. 2) | Pro-Pro-Lys-Ile-Tyr-Pro | 714.41 | 29.47 |
| HQMPKP (SEQ ID NO. 3) | His-Gln-Met-Pro-Lys-Pro | 737.37 | 41.84 |
| TSSLP (SEQ ID NO. 4) | Thr-Ser-Ser-Leu-Pro | 503.26 | 3.75 |

The material in the ASCI text file of the sequence listing of the above amino acid sequence SEQ ID No. 1, SEQ ID No, 2, SEQ ID No, 3 and SEQ ID No. 4 is herewith incorporated by reference. The ASCI text file was created on Jun. 30, 2022, and has a file name "LPTF2721-CNPC-TUSP202101826 Replacement Sequence Listing" and a size of 839 bytes. Table 7 Identification Results of Oxidation Resistance of Selenium-Chelating Pea Oligopeptide and Peptide Segments

TABLE 7

Identification results of oxidation resistance of selenium-chelating pea oligopeptide and peptide segments

| Type | Total antioxidant capacity (mmol/mg) | Increased multiple, compared with selenium-chelating pea oligopeptide |
|---|---|---|
| Selenium-chelating pea oligopeptide | 54.13 | |
| TGRGAP (SEQ ID NO: 1) | 3.25 | 0.06 |
| PPKIYP (SEQ ID NO: 2) | 211.12 | 3.90 |
| HQMPKP (SEQ ID NO: 3) | −9.53 | — |
| TSSLP (SEQ ID NO :4) | 5.55 | 0.10 |

Experimental Example 1 Effect of Reaction Temperature on Chelation Result

The concentration of the pea oligopeptide aqueous solution was 1% (i.e., 1 g/100 mL), the mass ratio (peptide-salt mass ratio) of the pea oligopeptide to the sodium selenite was 2:1, the pH value was 8.5, reaction was carried out at 60, 70, 80, 85, 90° C., respectively, for 30 min to investigate the effect of reaction temperature on the yield and the chelation rate.

Figure 27:
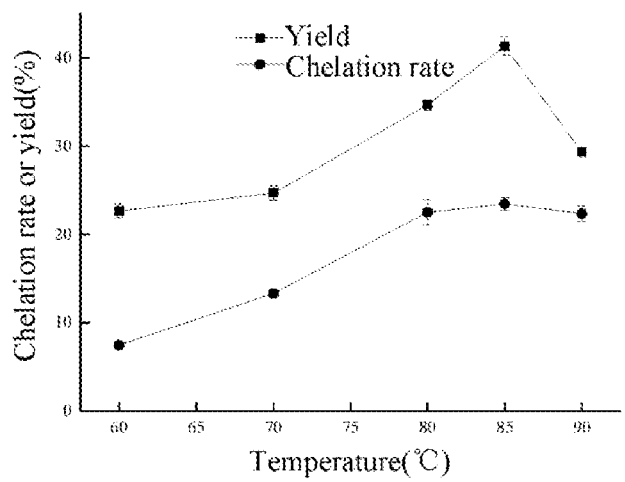
FIG. 27 shows an influence of a temperature on a chelation reaction in Experimental Example 1.

As shown in FIG. 27, temperature had a great influence on the chelation reaction, and as the temperature increased, both the chelation rate and the yield gradually increased, indicating that the increase in temperature facilitated the chelation process. When the temperature exceeded 85° C., the yield gradually decreased. But the chelation rate remained basically unchanged, indicating that an excessive high temperature would also prevent the reaction from proceeding. Through variance analysis, the yield of 85° C. group had significant difference from that of 80° C. group, and had extremely significant difference from that of other group (except 80° C.); chelation rate of 85° C. group had no significant difference from chelation rates of 80° C. and 90° C. groups, and had extremely significant difference from that of other group (except 80° C., 90° C.). Therefore, the reaction temperature was generally controlled to be 70-90° C., preferably 80-85° C.

Experimental Example 2 Research of Effects of Peptide-Salt Mass Ratio on Chelation Result The concentration of the pea oligopeptide aqueous solution was 1% (i.e., 1 g/100 mL), the pH value was 8.5, the reaction temperature was set to be 85° C., reaction was carried out at peptide-salt mass ratios of 1:1, 2:1, 3:1, 4:1, 5:1, respectively, for 30 min to investigate the effects of peptide-salt mass ratio on the yield and the chelation rate.

Figure 28:
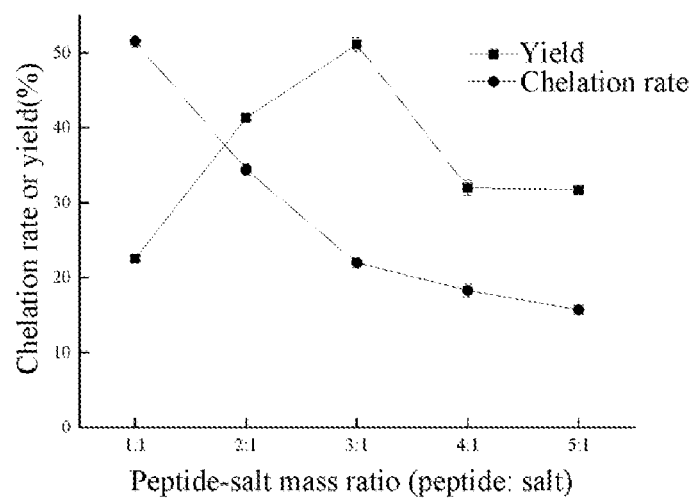
FIG. 28 shows an influence of a peptide-salt mass ratio on a chelation reaction in Experimental Example 2.

As shown in FIG. 28, with the gradual increase of the peptide-salt mass ratio, the chelation rate gradually decreased, but the yield gradually increased, change trends of the two indicators were opposite; with the increase of the peptide-salt mass ratio, concentration of the peptide remained unchanged, the mass of the salt decreased. The decrease of the mass of the salt was the main reason for the decrease of the chelation rate. However, when the peptide-salt mass ratio exceeded 3:1, the yield of the product also showed a downward trend, while a downward trend of the chelation rate gradually became flat. The peptide-salt mass ratio of 3:1 was the condition having the highest yield of chelation. Through variance analysis, the yield and the chelation rate of 3:1 group had extremely significant difference from those of other group. The mass ratio of pea oligopeptide to sodium selenite was generally controlled to be 2-4:1.

Experimental Example 3 Effects of Peptide Concentration on Yield and Chelation Rate The peptide-salt mass ratio was 3:1, the chelation pH value was 8.5 and the chelation temperature was set to be 85° C., reaction was carried out for 30 min under conditions where the concentrations of the pea oligopeptide aqueous solution were 2% (i.e., 2 g/100 mL), 3% (i.e., 3 g/100 mL), 4% (i.e., 4 g/100 mL) and 5% (i.e., 5 g/100 mL), respectively, to investigate the effects of peptide concentration on the yield and the chelation rate.

Figure 29:
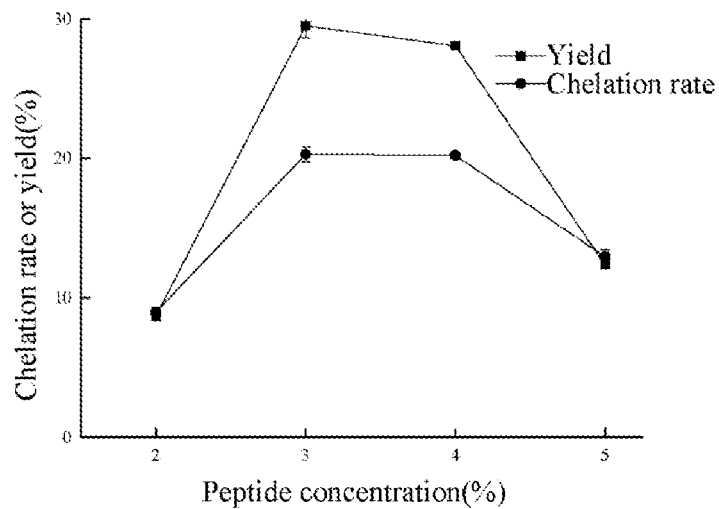
FIG. 29 shows an influence of a pea oligopeptide concentration on a chelation reaction in Experimental Example 3.

As shown in FIG. 29, with the increase of the concentration of the pea oligopeptide aqueous solution, both the chelation rate and the yield showed a change trend of increasing firstly, stabilizing subsequently, and decreasing finally. Through variance analysis, the yield and the chelation rate at the peptide concentration of 3% had extremely significant difference from the two indicators of other group (except 4%), and had no significant different difference from the two indicators of 4% group. Therefore, the concentration of the pea oligopeptide aqueous solution was generally controlled to be 3-5 g/100 mL.

Experimental Example 4 Effects of pH Value in Reaction on Yield and Chelation Rate The concentration of the pea oligopeptide aqueous solution was designed to be 4% (4 g/100 mL), the peptide-salt mass ratio was 3:1, the chelating temperature was set to be 85° C., reaction was carried out for 30 min at chelation pH of 6.5, 7, 8, 8.5, 9 respectively to investigate the effects of pH in the reaction on the yield and the chelation rate.

Figure 30:
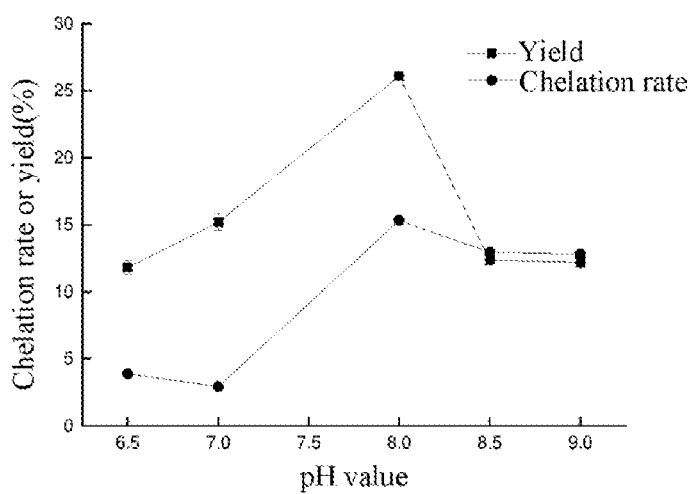
FIG. 30 shows an influence of a pH value on a chelation reaction in Experimental Example 4.

As shown in FIG. 30, with the increase of the pH value of the solution, both the chelation rate and the yield showed an increasing trend in their entireties, but after the pH exceeded 8, the two indicators showed a downward trend and gradually flattened. This indicated that the chelation reaction had a better reaction result under a weak alkaline environment. Through variance analysis, when pH was 8, both the yield and the chelation rate had extremely significant difference from those of other group. In fact, when the pea oligopeptide and the sodium selenite were completely dissolved, the pH of the solution was about 8.

Experimental Example 5 Effects of Reaction Time on Yield and Chelation Rate

The concentration of the pea oligopeptide aqueous solution was 4% (4 g/100 mL), the peptide-salt mass ratio was 3:1, the chelation temperature was set to be 85° C., the chelation pH was 8.5, reaction was carried out for 20, 30, 40, 50, 60 min, respectively, to investigate the effects of reaction time on the yield and the chelation rate.

Figure 31:
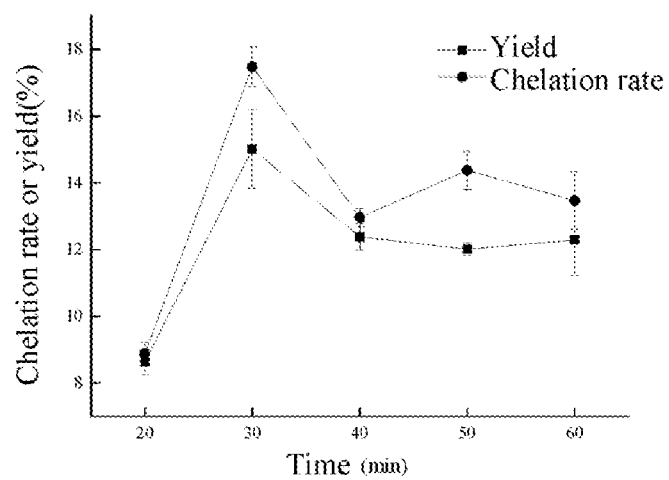
FIG. 31 shows an influence of reaction time on a chelation reaction in Experimental Example 5.

As shown in FIG. 31, with the extension of the chelation time, both the chelation rate and the yield gradually increased. When the chelation time exceeded 30 minutes, both the chelation rate and the yield decreased, and stabilized within a certain range of fluctuation. Through variance analysis, the yield and the chelation rate of 30 min group had extremely significant difference from the two indicators of 20 min group, and had significant difference from those of other group (except the 20 min group). There was no significant difference in the two indicators between the 40, 50, and 60 min groups.

The above embodiments are only used to describe the technical solutions of the present disclosure; those skilled in the art can still modify the technical solutions described in the foregoing embodiments, or make equivalent substitutions to some or all of the technical features therein; and these modifications or substitutions will not make the essentials of the corresponding technical solutions depart from the scope of the technical solutions in the embodiments of the present disclosure.

What is claimed is:

1. A selenium-pea oligopeptide chelate, wherein the selenium-pea oligopeptide chelate contains an amino acid sequence of SEQ ID NO:2, and a mass content of SEQ ID NO:2 is not less than 25 ng/mg; acid soluble protein content of the selenium-pea oligopeptide chelate is more than 23%, total nitrogen content is more than 23%; the selenium-pea oligopeptide chelate is composition of selenium-pea oligopeptide chelate with different molecular weight, and a portion of selenium-pea oligopeptide chelate with molecular weight less than 1000 u accounts for more than 85% of a total amount of the selenium-pea oligopeptide chelate; and selenium content is not less than 0.08 g per 100 g of the selenium-pea oligopeptide chelate;

wherein the selenium-pea oligopeptide chelate is a reaction product of an aqueous solution of pea oligopeptide and sodium selenite, and selenium of the sodium selenite is stably combined with the pea oligopeptide in a way of covalent bond so that after the selenium-pea oligopeptide chelate is prepared and then subjected to digestion treatment in at least one of following three ways, a change rate of the selenium content is not more than 3% with respect to the selenium content before the digestion treatment:

hydrolyzing for 4 hours by a pepsin at a pH value of 2 and a temperature of 37° C.;

hydrolyzing for 6 hours by a trypsin at a pH value of 7.5 and a temperature of 37° C.;

maintaining a temperature constant at 37° C., and firstly hydrolyzing for 4 hours by a pepsin at a pH value of 2, and then continuing to hydrolyze for 6 hours by a trypsin at a pH value of 6.8;

wherein the change rate of the selenium content is a mass percentage of a mass of selenium decomposed during the digestion treatment of the selenium-pea oligopeptide chelate to a total mass of selenium in the selenium-pea oligopeptide chelate before the digestion treatment.

2. The selenium-pea oligopeptide chelate according to claim 1, wherein the selenium of the sodium selenite is stably combined with the pea oligopeptide in the way of covalent bond so that after the selenium-pea oligopeptide chelate is prepared and then subjected to heat treatment for 2 hours at 40° C.-100° C., the selenium content is more than 97% of that before the heat treatment.

3. The selenium-pea oligopeptide chelate according to claim 1, wherein the selenium of the sodium selenite is stably combined with the pea oligopeptide in the way of covalent bond so that after the selenium-pea oligopeptide chelate is prepared and then subjected to acidic treatment or alkaline treatment for 2 hours at a pH of 3-11 and a temperature of 37° C., the selenium content is more than 75% of that before the acidic treatment or alkaline treatment.

4. The selenium-pea oligopeptide chelate according to claim 1, wherein a preparation method of the pea oligopeptide comprises:

mixing a pea protein powder and water in a ratio of 1:8-12, adjusting a pH value of the resulting material liquid to 8-10, controlling a temperature to 40-60° C., and adding an alkaline protease and a neutral protease for enzymolysis, wherein dosage of each of the alkaline protease and the neutral protease is 1.0-3.0% of the mass of the pea protein powder, and enzymolysis time is 3-6 hours;

wherein components of the pea oligopeptide with molecular weight less than 1000 u account for more than 80% of the total amount of the pea oligopeptide; and in an aqueous solution of the pea oligopeptide, a mass concentration of the pea oligopeptide is 1-5 g/100 mL.

5. A preparation method of the selenium-pea oligopeptide chelate according to claim 1, comprising:

reacting a mixed system of an aqueous solution of pea oligopeptide and sodium selenite for more than 20 minutes at 60-90° C. to obtain a reaction product, which is then subjected to alcohol precipitation and drying to obtain the selenium-pea oligopeptide chelate.

6. The preparation method according to claim 5, wherein in the mixed system, a mass ratio of the pea oligopeptide to the sodium selenite is 1-5:1.

7. The preparation method according to claim 5, wherein in the pea oligopeptide, the pea oligopeptide is composition of pea oligopeptide with different molecular weight, and a content of components with molecular weight less than 1000 u is more than 80%; in the aqueous solution of the pea oligopeptide, a mass concentration of the pea oligopeptide is 1-5 g/100 mL.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Pisum sativum

<400> SEQUENCE: 1

Thr Gly Arg Gly Ala Pro
1               5

<210> SEQ ID NO 2
<211> LENGTH: 6
<212> TYPE: PRT
<213> ORGANISM: Pisum sativum

<400> SEQUENCE: 2

Pro Pro Lys Ile Tyr Pro
1               5

<210> SEQ ID NO 3
<211> LENGTH: 6
<212> TYPE: PRT
<213> ORGANISM: Pisum sativum

<400> SEQUENCE: 3

His Gln Met Pro Lys Pro
1               5

<210> SEQ ID NO 4
<211> LENGTH: 5
<212> TYPE: PRT
<213> ORGANISM: Pisum sativum

<400> SEQUENCE: 4

Thr Ser Ser Leu Pro
1               5

<210> SEQ ID NO 5
<211> LENGTH: 4
<212> TYPE: PRT
<213> ORGANISM: Pisum sativum

<400> SEQUENCE: 5

Gly Gly Tyr Arg
1
```